(12) United States Patent
Bhogal et al.

(10) Patent No.: US 11,040,363 B2
(45) Date of Patent: Jun. 22, 2021

(54) MODULAR DEVICE FOR CELL SPRAYING

(71) Applicant: RenovaCare Sciences Corp., New York, NY (US)

(72) Inventors: Jatinder S. Bhogal, Vancouver (CA); Frank Schubert, Berlin (DE); Thomas Bold, Berlin (DE)

(73) Assignee: RenovaCare Sciences Corp., Roseland, NJ (US)

( * ) Notice: Subject to any disclaimer, the term of this patent is extended or adjusted under 35 U.S.C. 154(b) by 0 days.

(21) Appl. No.: 16/310,108

(22) PCT Filed: Jun. 13, 2017

(86) PCT No.: PCT/US2017/037274
§ 371 (c)(1),
(2) Date: Dec. 14, 2018

(87) PCT Pub. No.: WO2017/218549
PCT Pub. Date: Dec. 21, 2017

(65) Prior Publication Data
US 2019/0321837 A1    Oct. 24, 2019

Related U.S. Application Data

(60) Provisional application No. 62/349,979, filed on Jun. 14, 2016.

(51) Int. Cl.
*B05B 9/01* (2006.01)
*A61M 11/00* (2006.01)
(Continued)

(52) U.S. Cl.
CPC ............... *B05B 9/01* (2013.01); *A61B 90/08* (2016.02); *A61L 27/3687* (2013.01);
(Continued)

(58) Field of Classification Search
CPC .. A61L 27/3687; A61M 11/007; A61M 11/02; A61M 2205/75; A61M 2209/06;
(Continued)

(56) References Cited

U.S. PATENT DOCUMENTS

| 4,240,422 A | 12/1980 | Hazen |
| 5,139,031 A | 8/1992 | Guirguis |

(Continued)

FOREIGN PATENT DOCUMENTS

| CN | 104814768 A | 8/2015 |
| CN | 109562399 | 4/2019 |

(Continued)

OTHER PUBLICATIONS

"Bluetooth", Computer Desktop Encyclopedia 1981-2013, The Computer Language Inc., [Online]. [Archived Jun. 10, 2013]. Retrieved from the Internet: URL: http: encyclopedia2.thefreedictionary.com Bluetooth, (1981), 3 pgs.

(Continued)

*Primary Examiner* — Deanna K Hall
(74) *Attorney, Agent, or Firm* — Schwegman Lundberg & Woessner, P.A.

(57) ABSTRACT

Systems and methods for spraying a liquid treatment solution include a syringe attachment device and a handheld device. The syringe attachment device can be configured to secure a syringe containing the liquid treatment solution. The handheld device can have a movable slide configured to dispense the treatment solution from the syringe. The spray deposition system can include a cover' positioned to provide an impervious barrier between at least a portion of the syringe attachment device and the handheld device. The cover can be attached to the syringe attachment device prior to coupling the devices together. In an example, the cover can have a generally tubular shape with a closed end and an (Continued)

open end. The handheld device can be inserted into the cover and the cover can enclose the handheld device in the assembled position. In an example, the cover can be sterile and at least a portion of the syringe attachment device can be sterile.

27 Claims, 9 Drawing Sheets

(51) Int. Cl.
    *A61B 90/00*     (2016.01)
    *A61L 27/36*     (2006.01)
    *A61M 35/00*     (2006.01)

(52) U.S. Cl.
    CPC .... *A61M 11/007* (2014.02); *A61B 2090/0813* (2016.02); *A61L 27/362* (2013.01); *A61M 35/00* (2013.01); *A61M 2205/75* (2013.01); *A61M 2205/8206* (2013.01)

(58) Field of Classification Search
    CPC ....... A61M 35/00; A61M 35/003; B05B 9/01; B05B 7/02; A61B 90/40
    See application file for complete search history.

(56) References Cited

U.S. PATENT DOCUMENTS

| | | |
|---|---|---|
| 5,376,079 A | 12/1994 | Holm |
| 5,571,083 A | 11/1996 | Lemelson |
| 5,584,807 A | 12/1996 | McCabe |
| 5,810,885 A | 9/1998 | Zinger |
| 6,020,196 A | 2/2000 | Hu et al. |
| 6,047,861 A | 4/2000 | Vidal et al. |
| 6,117,150 A | 9/2000 | Pingleton et al. |
| 6,479,052 B1 | 11/2002 | Marshall et al. |
| 7,628,780 B2 | 12/2009 | Bonner et al. |
| 7,641,898 B2 | 1/2010 | Lyles |
| 7,833,522 B2 | 11/2010 | Dixon |
| 8,157,817 B2 | 4/2012 | Bonadio et al. |
| 8,529,957 B2 | 9/2013 | Turzi et al. |
| 8,790,680 B2 | 7/2014 | Chancellor et al. |
| 8,911,997 B2 | 12/2014 | Upton et al. |
| 9,505,000 B2 | 11/2016 | Bornemann |
| 9,510,910 B2 | 12/2016 | Miller et al. |
| 9,610,430 B2 | 4/2017 | Bornemann et al. |
| 10,376,658 B2 | 8/2019 | Bornemann |
| 2002/0082563 A1* | 6/2002 | Petersen ........... A61M 5/31581 604/191 |
| 2002/0082692 A1 | 6/2002 | Van Blitterswijk et al. |
| 2002/0106353 A1 | 8/2002 | Wood et al. |
| 2002/0165483 A1 | 11/2002 | Miller et al. |
| 2003/0202965 A1 | 10/2003 | Seubert et al. |
| 2004/0043007 A1 | 3/2004 | Andree et al. |
| 2004/0185091 A1 | 9/2004 | Truong-le et al. |
| 2004/0219133 A1 | 11/2004 | Lyles |
| 2005/0003524 A1 | 1/2005 | Gerlach et al. |
| 2005/0003535 A1 | 1/2005 | Gerlach |
| 2005/0015064 A1 | 1/2005 | Gerlach et al. |
| 2005/0032218 A1 | 2/2005 | Gerlach |
| 2005/0177098 A1 | 8/2005 | Lin et al. |
| 2006/0141616 A1 | 6/2006 | Guu et al. |
| 2007/0042488 A1 | 2/2007 | Bornemann |
| 2008/0038298 A1 | 2/2008 | Barnikol-keuten et al. |
| 2008/0140088 A1 | 6/2008 | Orban, III |
| 2008/0210246 A1 | 9/2008 | Johansson et al. |
| 2009/0191631 A1 | 7/2009 | Bornemann |
| 2009/0196855 A1 | 8/2009 | Bornemann |
| 2009/0248039 A1 | 10/2009 | Cooper et al. |
| 2009/0264831 A1 | 10/2009 | Thompson et al. |
| 2009/0317439 A1 | 12/2009 | Turzi et al. |
| 2010/0280312 A1 | 11/2010 | D'alessio et al. |
| 2011/0104280 A1* | 5/2011 | Hnojewyj ............. A61K 47/34 424/486 |
| 2013/0060335 A1* | 3/2013 | Bornemann ......... A61M 11/007 623/15.12 |
| 2013/0274609 A1 | 10/2013 | Glynn et al. |
| 2014/0107621 A1 | 4/2014 | Bornemann |
| 2014/0343454 A1 | 11/2014 | Miller et al. |
| 2015/0079153 A1 | 3/2015 | Quick et al. |
| 2017/0196679 A1 | 7/2017 | Bornemann |
| 2017/0304600 A1 | 10/2017 | Bornemann |
| 2019/0133706 A1 | 5/2019 | Bold et al. |
| 2020/0061311 A1 | 2/2020 | Bornemann |

FOREIGN PATENT DOCUMENTS

| | | |
|---|---|---|
| DE | 19964113 | 7/2001 |
| DE | 102007040252 | 6/2008 |
| DE | 102011100450 | 10/2012 |
| DE | 102011100450 | 7/2013 |
| DE | 102011100450 | 10/2013 |
| DE | 102013226253 | 6/2015 |
| DE | 102014117407 | 6/2016 |
| EP | 0809976 | 12/1997 |
| EP | 0809976 | 5/2003 |
| EP | 2049130 | 4/2009 |
| EP | 1664280 | 1/2011 |
| EP | 1357922 | 5/2011 |
| IN | 201917001073 | 3/2019 |
| JP | H08280697 | 10/1996 |
| JP | 2005218376 | 8/2005 |
| JP | 2006034719 | 2/2006 |
| JP | 2007507317 | 3/2007 |
| JP | 2012110514 | 6/2012 |
| WO | 02062358 | 8/2002 |
| WO | 2009017321 | 2/2009 |
| WO | 2009061915 | 5/2009 |
| WO | 2010126586 | 11/2010 |
| WO | 2013051816 | 4/2013 |
| WO | 2013075204 | 5/2013 |
| WO | 2015078137 | 6/2015 |
| WO | 2015142814 | 9/2015 |
| WO | WO-2015154188 A1 | 10/2015 |
| WO | 2017218549 | 12/2017 |

OTHER PUBLICATIONS

"Hartmann's solution", Saunders Comprehensive Veterinary Dictionary Elsevier, Inc., [Online]. [Archived Jun. 10, 2013]. Retrieved from the Internet: URL: http: medical-dictionary.thefreedictionary.com Hartmann's+Solution, (2007), 2 pgs.

"U.S. Appl. No. 11/518,012, Non Final Office Action dated Aug. 7, 2007", 9 pgs.

"U.S. Appl. No. 11/518,012, Response filed Dec. 22, 2011 to Non Final Office Action dated Aug. 7, 2007", 13 pgs.

"U.S. Appl. No. 11/518,012, Notice of Non-Compliant Amendment dated Jan. 29, 2013", 3 pgs.

"U.S. Appl. No. 11/518,012, Response filed Feb. 28, 2013 to Notice of Non-Compliant Amendment dated Jan. 29, 2013", 10 pgs.

"U.S. Appl. No. 11/518,012, Final Office Action dated Jun. 21, 2013", 15 pgs.

"U.S. Appl. No. 14/136,681, Preliminary Amendment dated Apr. 21, 2014", 8 pgs.

"U.S. Appl. No. 13/573,003, Preliminary Amendment dated Apr. 21, 2014", 7 pgs.

"U.S. Appl. No. 13/573,003, Non Final Office Action dated Jul. 22, 2015", 16 pgs.

"U.S. Appl. No. 14/136,681, Non Final Office Action dated Aug. 25, 2015", 10 pgs.

"U.S. Appl. No. 13/573,003, Response filed Jan. 22, 2016 to Non Final Office Action dated Jul. 22, 2015", 26 pgs.

"U.S. Appl. No. 13/573,003, Final Office Action dated Feb. 18, 2016", 17 pgs.

"U.S. Appl. No. 14/136,681, Response filed Feb. 23, 2016 to Non Final Office Action dated Aug. 25, 2015", 15 pgs.

"U.S. Appl. No. 14/136,681, Final Office Action dated Jun. 1, 2016", 11 pgs.

(56) References Cited

OTHER PUBLICATIONS

"U.S. Appl. No. 13/573,003, Response filed Aug. 3, 2016 to Final Office Action dated Feb. 18, 2016", 10 pgs.
"U.S. Appl. No. 13/573,003, Examiner Interview Summary dated Aug. 5, 2016", 3 pgs.
"U.S. Appl. No. 13/573,003, Notice of Allowance dated Aug. 22, 2016", 8 pgs.
"U.S. Appl. No. 13/573,003, Notice of Allowance dated Sep. 8, 2016", 5 pgs.
"U.S. Appl. No. 14/136,681, Response filed Nov. 1, 2016 to Final Office Action dated Jun. 1, 2016", 10 pgs.
"U.S. Appl. No. 14/136,681, Notice of Allowance dated Nov. 25, 2016", 7 pgs.
"U.S. Appl. No. 14/136,681, Notice of Allowance dated Feb. 10, 2017", 7 pgs.
"U.S. Appl. No. 15/360,230, Preliminary Amendment dated Apr. 5, 2017", 4 pgs.
"U.S. Appl. No. 15/360,230, Preliminary Amendment filed May 25, 2017", 7 pgs.
"Declaration of Dr. Jeffrey W. Shupp", *Avita Medical Limited* v. *RenovaCare Sciences Corp.* U.S. Pat. No. 9,610,430 (Claims 1-11) Filed: Dec. 20, 2013Inter Partes Review No. IPR2017-01243, Avita Medical Limited Ex. 1007, 106 pgs.
"Ex Vivo Definition", Stedman's Online Medical Dictionary [Online]. Retrieved from the Internet: URL: http: www.stedmansonline.com popup.aspx?aid=5188026, Avita Medical Ltd. Ext. 1011, (Accessed Apr. 3, 2017), 1 pg.
"In Vitro Definition", Stedman's Online Medical Dictionary [Online]. Retrieved from the Internet: URL: http: www.stedman son 1 ine .com popup.aspx ?a id= 5 200863, Avita Medical Ltd. Ex. 1012, (Accessed Apr. 3, 2017), 1 pg.
"Airbrush", Wikipedia—[Online]. Retrieved from the Internet: URL: https: en. wikiped ia.org wiki Airbrush, Avita Medical Ltd. Ex. 1015, (Accessed Mar. 26, 2017), 7 pgs.
"Human Skin", Wikipedia—[Online]. Retrieved from the Internet: URL: https: en. wikiped ia.org wiki Human _ skin, Avita Medical, Ltd. Ex 1013, (Accessed Mar. 28, 2017), 11 pgs.
"Apparatus and Method to Treat a Burn Injury", U.S. Appl. No. 60/705,906 to Dixon, (filed Aug. 5, 2005), 15 pgs.
"File History of the '430 patent (excluding non-patent literature and foreign references)", 268 pgs.
"International Application Serial No. PCT US2017 037274, International Search Report dated Aug. 31, 2017", 3 pgs.
"International Application Serial No. PCT US2017 037274, Written Opinion dated Aug. 31, 2017", 9 pgs.
"U.S. Appl. No. 15/360,230, Non Final Office Action dated Feb. 2, 2018", 20 pgs.
"Inter Partes Review No. IPR2017-01243 re. U.S. Pat. No. 9,610,430 (Claims 1-11)", *Avita Medical Limited* v. *RenovaCare Sciences Corp*. U.S. Pat. No. 9,610,430 (Claims 1-11), Patent Owner Renovacare Science Corp.'s Preliminary Response, Filed: Sep. 19, 2017, 63 pgs.
"Inter Partes Review No. IPR2017-01243 re. U.S. Pat. No. 9,610,430 (Claims 1-11)", *Avita Medical Limited* v. *RenovaCare Sciences Corp*. U.S. Pat. No. 9,610,430 (Claims 1-11), Decision Denying Institution of Inter Partes Review, Entered: Dec. 18, 2017, 9 pgs.
"U.S. Appl. No. 15/447,918, Preliminary Amendment filed Feb. 13, 2018", 6 pgs.
"U.S. Appl. No. 15/447,918, Non Final Office Action dated May 9, 2018", 12 pgs.
"U.S. Appl. No. 15/360,230, Response filed Aug. 2, 2018 to Non Final Office Action dated Feb. 2, 2018", 13 pgs.
"U.S. Appl. No. 15/360,230, Final Office Action dated Sep. 26, 2018", 18 pgs.
"U.S. Appl. No. 15/447,918, Response filed Nov. 9, 2018 to Non Final Office Action dated May 9, 2018", 14 pgs.
"U.S. Appl. No. 13/036,569 File History Portions Declarations and Application Filing Receipt", 7 pages.
"Declaration of Dr. Gary D. Shipley", (Dec. 19, 2017), 53 pages.
"Ex Parte Borgwardt, Appeal 2012-009099 PTAB Oct. 14, 2014", 5 pages.
"Ex Parte Jorgen J. Moller, Appeal No. 2010-012534 BPAI Jan. 27, 2011", 13 pages.
"Ex1008_ShuppCV", 37 pages.
"*GrowlerWerks, Inc.* v. *Drink Tanks Corporation*, IPR2016-01125, Paper No. 8 PTAB Nov. 22, 2016", (Nov. 22, 2016), 9 pages.
"International Application Serial No. PCT EP2017 064094, International Search Report dated Aug. 2, 2017", (Aug. 2, 2017), 4 pgs.
"European Application Serial No. 16174336.4 Extended European Search Report dated Nov. 28, 2016", (Nov. 28, 2016), 9 pgs.
"U.S. Appl. No. 16/309,726, Preliminary Amendment filed Dec. 13, 2018", 8 pgs.
"International Application Serial No. PCT EP2017 064094, International Preliminary Report on Patentability dated Dec. 18, 2018", (Dec. 18, 2018), 8 pages.
"U.S. Appl. No. 15/447,918, Non Final Office Action dated Mar. 26, 2019", 12 pages.
"U.S. Appl. No. 15/360,230, Response filed Mar. 26, 2019 to Final Office Action dated Sep. 26, 2018", 12 pages.
"U.S. Appl. No. 15/360,230, Examiner Interview Summary dated May 13, 2019", 3 pages.
"U.S. Appl. No. 15/360,230, Notice of Allowance dated May 24, 2019", 12 pgs.
"U.S. Appl. No. 15/360,230, Corrected Notice of Allowability dated Jun. 26, 2019", 2 pgs.
"European Application Serial No. 17813943.2, Response Filed Aug. 8, 2019 to Communication pursuant to Rules 161(2) and 162 EPC dated Jan. 19, 2019", 13 pgs.
"U.S. Appl. No. 15/447,918, Response filed Aug. 26, 2019 to Non-Final Office Action dated Mar. 26, 2019", 12 pgs.
"Australian Application Serial No. 2017283496, First Examination Report dated Aug. 28, 2019", 3 pages.
"European Application Serial No. 16174336.4 Office Action dated Oct. 22, 2019", 4 pages.
"U.S. Appl. No. 15/447,918, Final Office Action dated Dec. 12, 2019", 13 pages.
"Canadian Application Serial No. 3,027,493, Office Action dated Dec. 17, 2019", 5 pages.
"European Application Serial No. 17813943.2, Extended European Search Report dated Jan. 30, 2020", 8 pages.
"Japanese Application Serial No. 2018-566399, Notification of Reasons for Rejection dated Feb. 3, 2020", with English translation, 11 pages.
"U.S. Appl. No. 16/459,205, Preliminary Amendment filed Mar. 13, 2020", 7 pages.
"Canadian Application Serial No. 3,027,493, Response filed Apr. 17, 2020 to Office Action dated Dec. 17, 2019", 19 pages.
U.S. Appl. No. 15/447,918, Response filed May 12, 2020 to Final Office Action dated Dec. 12, 2019, 12 pages.
"Ringer solution", Farlex Partner Medical Dictionary, Farlex, [Online]. [Archived Jun. 10, 2013]. Retrieved from the Internet: URL: http: medical-dictionary.thefreedictionary.com Ringer+lactate, (2012), 2 pgs.
"Skin Cell Gun", Wikipedia, [Online]. Retrieved from the Internet: URL: http: en.wikipedia.org wiki Skin_cell_gun, (Accessed Apr. 22, 2014), 5 pgs.
"Respiratory Failure and Stimulation of Glycolysis in Chinese Hamster Ovary Cells Exposed to Normobaric Hyperoxia*", The Journal of Biological Chemistry 265(19), (1990), 11118-11124.
"WO2015078137 A1", Google Translation, [Online] Retrieved from the Internet: URL:https: patents.google.com patent WO2015078137A1 en, (Reterived Jan. 18, 2017), 7 pgs.
"WO2013051816 A2", Google Translations, (Reterived Jan. 18, 2017), 14 pgs.
"Petition for Inter Partes Review No. IPR2017-01243 re. U.S. Pat. No. 9,610,430 (Claims 1-11)", *Avita Medical Limited* v. *RenovaCare Sciences Corp*. U.S. Pat. No. 9,610,430 (Claims 1-11) Filed: Dec. 20, 2013, 81 pgs.
"Nozzle", Wikipedia—[Online]. Retrieved from the Internet: URL: https : en. wiki ped ia.org wiki Nozzle, Avita Medical, Ltd. Ex. 1014, (Accessed Mar. 26, 2017), 4 pgs.
"IPR2017-01243 Notice of Accord Filing Date", (Apr. 24, 2017), 5 pages.

(56) References Cited

OTHER PUBLICATIONS

"IPR2017-01243 Order—Resetting Notice of Filing Date Accorded to Petition and Time for Filing Patent Owner Preliminary Response", (dated Jun. 26, 2017), 5 pages.
"IPR2017-01243 Patent Owner's Mandatory Notices", (May 5, 2017), 5 pages.
"Resume of Dr. Shipley", 6 pages.
"IPR2017-01243 Stipulation by Petitioner re Effective Filing Date of the Subject Patent", (Jul. 13, 2017), 2 pages.
"International Application Serial No. PCT EP2017 064094, Written Opinion dated Aug. 2, 2017", (Aug. 2, 2017), 6 pgs.
Balin, Arthur K, "Oxygen modulates growth of human cells at physiologic partial pressures", The Journal of Experimental Medicine 160(1), (Jul. 7, 1984), 152-166.
Esteban Vives, Roger, "Second-degree burns with six etiologies treated with autologous noncultured cell spray graftin", Burns 42, (2016), 8 pages.
Esteban-Vives, Roger, "Calculations for reproducible autologous skin cell-spray grafting", Burns, JBUR-4972, (2016), 10 pgs.
Gerlach, "Skin Cell Gun", Poster, [Online]. Retrieved from the Internet: URL: http: bethsumner.com wp-content uploads 2012 05 1338405697mmvrposter.jpg, (2012), 1 pg.
Gerlach, Jorg C, "Method for autologous single skin cell isolation for regenerative cell spray transplantation with non-cultured cells", Int J Artif Organs 34(3), 271-279.
Goetz, Ingeburg E, "Oxygen Toxicity in Normal and Neoplastic Hamster Cells in Culture", Society for inn Vitro Biology 11(6), (1975), 382-394.
Hartmann, Bernd, "Sprayed cultured epithelial autografts for deep dermal burns of the face and neck", Ann Plast Surg. 58(1), (2007), 70-73.
Herndon, David N, "Comparison of cultured epidermal autograft and massive excision with serial autografting plus homograft overlay", J Burn Care Rehabil 13(1), (1992), 154-157.
Johnen, C., "Skin cell isolation and expansion for cell transplantation is limited in patients using tobacco, alcohol, or are exhibiting diabetes mellitus", Burns, 32(2), (Mar. 2006), 194-200.
Kazzaz, Jeffery A, "Cellular Oxygen Toxicity. Oxidant Injury Without Apoptosis*", The Journal of Biological Chemistry 271(25), (1996), 15182-15186.
Lawlor, Kynan T., "Dermal Contributions to Human Interfollicular Epidermal Architecture and Self-Renewal", International Journal of Molecular Sciences, Avita Medical, Ltd. Ex. 1010, (Nov. 25, 2015), 10 pgs.
Michiels, Carine, "Comparative Study of Oxygen Toxicity in Human Fibroblasts and Endothelial Cells", Journal of Cellular Physiology 144(2), (Aug. 1990), 295-302.
Navarro, F. A, "Sprayed Keratinocyte Suspensions Accelerate Epidermal Coverage in a Porcine Microwound Model", Journal of Burn Care and Rehabilitation, 21(6), (Nov. Dec. 2000), 513-518.
Wood, F. M, "The use of cultured epithelial autograft in the treatment of major burn wounds: Eleven years of clinical experience", Burns, 32(5), (2006), 538-544.
Wood, Fiona, "Clinical Potential of Autologous Epithelial Suspension", Wounds 15(1), (2003), 16-22.

International Application Serial No. PCT/US2017/037274, International Preliminary Report on Patentability dated Dec. 27, 2018, 11 pages.
U.S. Appl. No. 16/459,205, filed Jul. 1, 2019, Device for Cell Spraying.
"Australian Application Serial No. 2017283496, Response filed Jun. 4, 2020 to First Examination Report dated Aug. 28, 2019", 25 pages.
"Canadian Application Serial No. 3,027,493, Office Action dated Jul. 16, 2020", 3 pages.
"European Application Serial No. 17813943.2, Response filed Aug. 19, 2020 to Extended European Search Report dated Jan. 30, 2020", 12 pgs.
"Indian Application Serial No. 201917001073, First Examination Report dated Jul. 2, 2020", with English translation, 8 pages.
"Japanese Application Serial No. 2018-566399, Response filed May 7, 2020 to Notification of Reasons for Rejection dated Feb. 3, 2020", with English claims, 12 pages.
"Chinese Application Serial No. 201780045407.8, Office Action dated Aug. 24, 2020", with English translation, 21 pages.
"Canadian Application Serial No. 3,027,493, Response filed Sep. 11, 2020 to Office Action dated Jul. 16, 2020", 11 pgs.
"U.S. Appl. No. 16/309,726, Restriction Requirement dated Oct. 7, 2020", 6 pgs.
"Korean Application Serial No. 10-2019-7001235, Notice of Preliminary Rejection dated Oct. 5, 2020", with English translation, 12 pages.
"Japanese Application Serial No. 2018-566399, Notification of Reasons for Refusal dated Oct. 26, 2020", with English translation, 7 pages.
U.S. Appl. No. 17/143,131, filed Jan. 6, 2021, Modular Device for Cell Spraying.
"U.S. Appl. No. 15/447,918, Non Final Office Action dated Mar. 2, 2021", 15 pgs.
"Indian Application Serial No. 201917001073, Response filed Feb. 26, 2021 to First Examination Report dated Jul. 2, 2020", with English claims, 28 pages.
"Chinese Application Serial No. 201780045407.8, Response filed Mar. 8, 2021 to Office Action dated Aug. 24, 2020", with English claims, 23 pages.
"Japanese Application Serial No. 2018-566399, Response filed Mar. 26, 2021 to Notification of Reasons for Refusal dated Oct. 26, 2020", with English claims, 14 pages.
"U.S. Appl. No. 16/309,726, Response filed Apr. 19, 2021 to Non Final Office Action dated Jan. 21, 2021", 13 pgs.
"European Application Serial No. 16174336.4 Response Filed Feb. 27, 2020 to Office Action dated Oct. 22, 2019", (Feb. 27, 2020), 18 pgs.
"European Application Serial No. 16174336.4, Decision to Grant dated Sep. 3, 2020", (Sep. 3, 2020), 2 pgs.
"U.S. Appl. No. 16/309,726, Non Final Office Action dated Jan. 21, 2021", 13 pgs.
"Chinese Application Serial No. 201780037091.8, Office Action dated Jan. 13, 2021", with English translation, (Jan. 13, 2021), 13 pages.

* cited by examiner

MODULAR DEVICE FOR CELL SPRAYING

CLAIM OF PRIORITY

This patent application is a U.S. national stage application filed under 35 U.S.C. § 371 from International Application Ser. No. PCT/US2017/037274, filed on Jun. 13, 2017 and published as WO 2017/218549 on Dec. 21, 2017, which claims the benefit of priority of U.S. Provisional Patent Application Ser. No. 62/349,979, filed on Jun. 14, 2016. The above applications are incorporated herein by reference in their entireties.

BACKGROUND

Spraying of cells may be of interest for the distribution of cell suspensions on a specific surface, such as, for example, a tissue wound. The spraying of cells is used, for example, in surgery in order to regenerate traumatized tissue. In many scenarios, it is beneficial or critical that the deposition system for the cells be sterile. Although the cell deposition or spraying can be done manually, an electrically operated and electronically controlled device can allow for controlled application of the cells onto the surface. Such devices can have a motor drive, a battery and other components. It can be difficult to sterilize portions of these devices since the sterilization process can potentially harm or destroy these components.

OVERVIEW

The present inventors have recognized, among other things, an opportunity for improved methods and systems for spraying a medical treatment solution on a living being, including an improvement in the ease of use of the system and methods of maintaining a sterile environment during spraying.

Examples according to the present application can include a spray deposition system having a syringe attachment device and a handheld device which are configured to be coupled together in an assembled position of the spray deposition system. In an example, one or both of the syringe attachment device and the handheld device can be sterile. In an example, both the syringe attachment device and the handheld device can be non-sterile. The syringe attachment device can include a base with a coupling portion and a top portion, a needle adjacent a syringe channel, the syringe channel configured to receive a syringe, and a tube having a discharge end proximate a delivery end of the needle, the tube configured to deliver an air flow. The handheld device can have an upper surface including a movable slide. The movable slide can be configured to dispense a treatment solution from the syringe contained within the syringe channel. In an example, the treatment solution and the syringe can be sterile. In an example, the treatment solution and the syringe can be non-sterile.

Examples according to the present application can include a spray deposition system having a syringe attachment device and a handheld device, as well as a cover positioned to provide an impervious barrier between at least a portion of the syringe attachment device and the handheld device. In an example, the cover can be attached to the syringe attachment device prior to coupling the syringe attachment device and the handheld device. In an example, the cover can have a generally tubular shape with a closed end and an open end. In an example, the handheld device can be inserted into the cover and the cover can enclose the handheld device in the assembled position. In an example, the cover can be sterile. In an example, the syringe attachment device can be sterile. In an example, the treatment solution can include autologous skin cells for treating a wound of a patient. In an example, the treatment solution can be sterile and delivered to the patient via a sterile syringe.

Examples according to the present application can include a method of spray depositing a treatment solution. In an example, the treatment solution can be sterile. In an example, the treatment solution can be non-sterile. The method can comprise providing a spray deposition system having a syringe attachment device configured to receive a syringe and a handheld device configured to be removably coupled to the syringe attachment device when the system is in an assembled position. The method can include creating a sterile barrier between at least a portion of the syringe attachment device and the handheld device, and inserting a syringe into the syringe attachment device, the syringe containing a treatment solution. The method can include spraying the treatment solution from the syringe attachment device.

Examples according to the present application can include a method of assembling a spray deposition system. The method can comprise coupling a syringe attachment device to a handheld device, inserting a syringe at least partially in a syringe channel of the syringe attachment device, coupling a needle adjacent the syringe channel with the syringe, coupling a plunger of the syringe with a movable slide of the handheld device, and at least partially surrounding the handheld device with a sterile cover positioned to provide an impervious barrier between at least a portion of the syringe attachment device and the handheld device.

Examples according to the present application can include a kit for treating a wounded area of skin on a living being. The kit can include a sterile syringe attachment device, a handheld device configured to be removably coupled to the syringe attachment device in an assembled position, and one or more materials for making a cell suspension of cells. The cell suspension can be contained within a syringe that can be received in the syringe attachment device. The handheld device in combination with the syringe attachment device can form a spray deposition system configured to deliver the cells from the syringe to the wounded area of a subject in need thereof. In an example, the subject can be a human. In an example, the subject can be a non-human animal. As used here, the term "subject" or "patient" can refer to a living being, including humans and animals. In an example, the kit can include a sterile cover for providing a sterile environment for the delivery of the cells. The sterile cover can be attached to the syringe attachment device prior to coupling the syringe attachment device to the handheld device. In an example, the sterile cover can be closed on one end and the handheld device can be inserted into an interior of the sterile cover and the open end of the sterile cover can then be sealed such that the handheld device can be contained within the sterile cover. In an example, the handheld device can be reusable and the syringe attachment device can be disposable after a single use.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
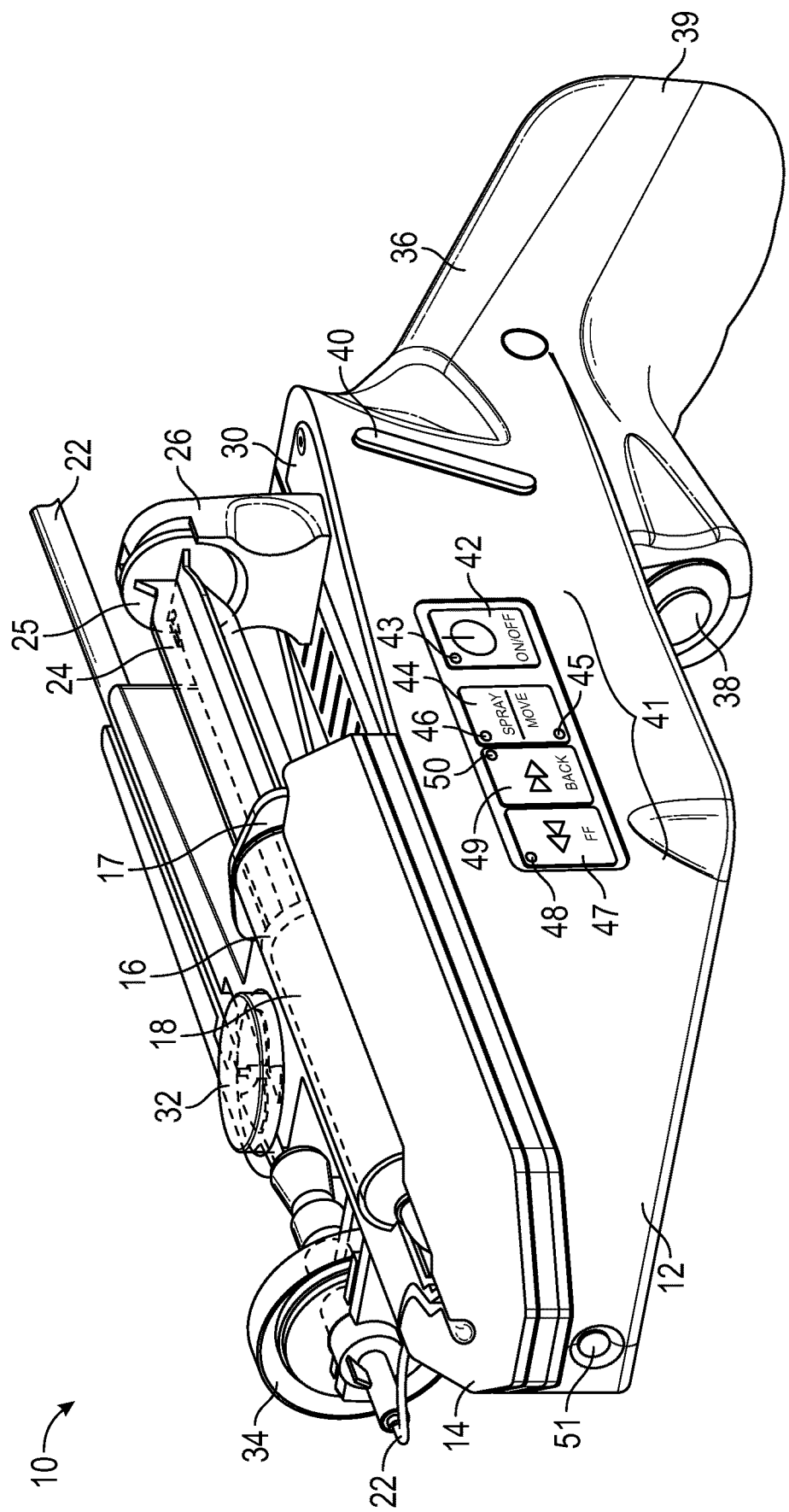
FIG. 1 is a perspective view of an example spray deposition system, in accordance with the present patent application.

The present application relates to spray deposition systems and methods for distributing a medical solution from a syringe. A spray deposition system of the present application can be a two part system having a handheld device and a syringe attachment device for housing the syringe. In an example, at least a portion of the syringe or the medical solution can be sterile. The spray deposition system can be configured to deliver the medical solution from the syringe to a subject, such as a human. The syringe attachment device can include one or more accessories to aid in delivery of the medical solution and can be pre-assembled for ease of use by the physician, clinician or other user. The syringe attachment device and handheld device can be releasably attached together. In an example, the syringe attachment device can be disposable after delivery of the medical solution and the handheld device can be reused.

In an example, the spray deposition system can be used for the delivery of cells, suspended in a solution, to skin. The cells in the suspension can be single cells, small cell aggregates, or a combination of single cells and small cell aggregates. For purposes herein, cell suspension or single-cell suspension generally refers to all or substantially all of the cells being single cells. However, it is recognized that, as a result of the cell preparation procedures, cells can occasionally remain stuck together and form small cell aggregates. Although cells in a suspension can be distributed or delivered in small quantities over a grafting area (via pipetting or dropping, injection syringe or other similar instruments), electrically operated and electronically controlled spray devices can allow for controlled application of such cells on wound surfaces. A manual cell sprayer can be sterilized without substantial difficulty since it comprises no electrical or electronic components. In contrast, automatic cell sprayers can have a motor drive, a battery and similar sensitive components, such as electrical wires, which can be damaged irreversibly during a sterilization process, such as by the effect of water, disinfectants or heat.

In an example, the spray deposition system can include a cover configured to provide a barrier between at least a portion of the syringe attachment device and the handheld device. The cover can be sterile or non-sterile. In many scenarios in which the medical solution is delivered to a patient or subject, it can be beneficial or critical that a portion of the system remain sterile. However, it can be challenging to sterilize portions of the system having electrical or electronic components since the sterilization process can have a risk of harming or destroying these components. The cover and the syringe attachment device, which can be sterile, can be preassembled together such that the cover can be attached to the syringe attachment device. Once the syringe attachment device and the handheld device are releasably coupled together, the cover can cover the handheld device such that the spray deposition system can be used in a sterile manner without sterilizing the handheld device. Such design, in which only a portion of the spray deposition system is covered, can be superior to other designs in which a cover can be placed over the entire spray deposition system to create a sterile environment. This type of whole system cover can be cumbersome and a potential source for malfunction of the system.

In an example, the spray deposition system can include non-sterile components. In such a case, the syringe that is contained within the syringe attachment device can be non-sterile. In an example, a non-sterile syringe can be used for animal subjects.

In an example, the spray deposition system of the present application can be used for a liquid treatment solution containing cells. The cells can be sprayed onto a living being to treat, for example, a tissue wound caused by a burn or other trauma. The spray deposition system can be used to provide rapid cell coverage in areas of tissue wounds, tissue trauma/injury and donor sites. The spray deposition system can reduce the size of skin cell donor sites, and the biopsy donor site can be smaller than a split skin graft donor site, and can reduce or eliminate the use of split skin graft donor sites. The spray deposition system can improve an expansion rate of cell coverage, improve the rate of healing of small burns, and can improve scar quality.

The spray deposition system, and methods associated therewith, can be used for the treatment of various skin disorders or diseases. For example, the various skin disorders and diseases can include, but are not limited to: epidermal resurfacing, replacement after skin loss, site match-up during re-pigmentation of an area of skin, treatment of burn wounds, leukoderma, vitiligo, piebaldism, in the treatment of scars (for example, scars caused through incorrect wound healing, improper scar direction or scar distortion from wound contraction, or acne scars), resurfacing cosmetic dermabrasion, resurfacing after laser treatment, and in association with dermal reconstruction. The spray deposition system can be used for cell replacement therapy, including but not limited to, nerve cell replacement treatment, epithelial cell (such as urothelial cell, buccal mucosal cell and respiratory epithelial cell) replacement treatment, endothelial cell replacement treatment, and osteogenic precursor cell replacement treatment. The spray deposition system can be used to stimulate tissue regeneration in surgically induced wounds.

The spray deposition system, and methods associated therewith, can be used to deliver a suspension of cells in a ratio to each other comparable with those seen in situ. This can be due, in part, to the manner of preparation of the cellular suspension, cells such as keratinocyte basal cells, Langerhans cells, fibroblasts and melanocytes typically have enhanced survival rates in comparison to standard tissue culture techniques, whereby selective cell culture can result in the loss of certain cell types. This can facilitate proper re-pigmentation of skin after a skin graft. The spray deposition system can facilitate faster surgery and healing, and can thereby reduce trauma for patients during the phase of their medical care.

The spray deposition system, including the cell suspension, can be used in combination with existing methods for treating skin wounds, including, for example, skin flap grafting, split kin grafting, mesh skin grafting, and cell sheets.

The present application focuses on the use of the spray deposition system for spraying autologous cells onto a wounded area of skin of a subject or patient. However, it is recognized that the spray deposition system can be used in other medical applications, including, but not limited to: (1) equipment intended to distribute an irrigation solution for wound cleaning by means of a spray head in a tissue-conserving manner (for example, unsterile medical spray equipment with a sterile disposable spray head which keeps a wound moist and/or cleans it); (2) equipment intended to apply a debridement solution for wound debridement, abrasively, by means of a pump (for example, unsterile pump apparatus with a sterile disposable spray head for surgical spray debridement or cutting equipment for medical split skin production with an unsterile drive part and a sterile disposable cutting component); (3) equipment intended to spray and distribute a solution from a medical Luer lock syringe, by means of a motor-driven piston pump, uniformly over a wound; and (4) equipment intended to spray treatment solutions comprising agents such as therapeutic drugs, antimicrobial agents, analgesics, and anti-inflammatory agents. In an example, one or more of the spray treatment solutions listed under (4) can be used in combination with a solution containing autologous cells.

In the medical applications listed above, the sterile cover described above can be well suited for use in the spray deposition system since the equipment used in those applications can include electrical, electromechanical, or electronic components.

FIGS. 1-6 illustrate an example spray deposition system 10 for delivering a medical treatment solution to a subject or patient. The spray deposition system 10 can have a two-part design including a handheld device 12 and a syringe attachment device 14. The handheld device 12 can also be referred to as a housing or controller. The handheld device 12 and the syringe attachment device 14 can be releasably coupled together, as shown in FIG. 1, and each of devices 12 and 14 can include one or more coupling features, as described below and shown in FIGS. 5 and 6.

The spray deposition system 10 is shown in FIG. 1 in an assembled position in which the handheld device 12 and the syringe attachment device 14 are coupled together, and the system 10 is ready for delivery of the medical treatment solution. FIGS. 2-6 show each of the devices 12 and 14 in an uncoupled or disassembled position and illustrate features of each of the respective devices 12 and 14.

In an assembled position, the spray deposition system 10 can include a syringe 16 disposed within a syringe channel 52 (see FIGS. 3 and 4) of the syringe attachment device 14, and the syringe 16 can contain a treatment solution 18. In an example, the treatment solution 18 can be a liquid suspension. The handheld device 12 can be configured to deliver the treatment solution 18 from the syringe 16 through a needle 20 (see FIG. 4). Air can be discharged through a tube or tubing 22 and exit the tube or tubing 22 at a discharge end (see FIG. 4). The needle 20 can pass through the tube or tubing 22 near the discharge end such that sterile air passing through the tube or tubing 22 can make contact with the liquid treatment solution 18 as it exits the needle 20, producing a fine spray of airborne droplets of the solution 18. In an example, the treatment solution 18 can be cells, such as, for example, autologous skin cells, and the airborne droplets from the spray deposition system 10 can be used, for example, for spraying cells onto a tissue wound. This is described further below in reference to FIG. 16.

Figure 2:
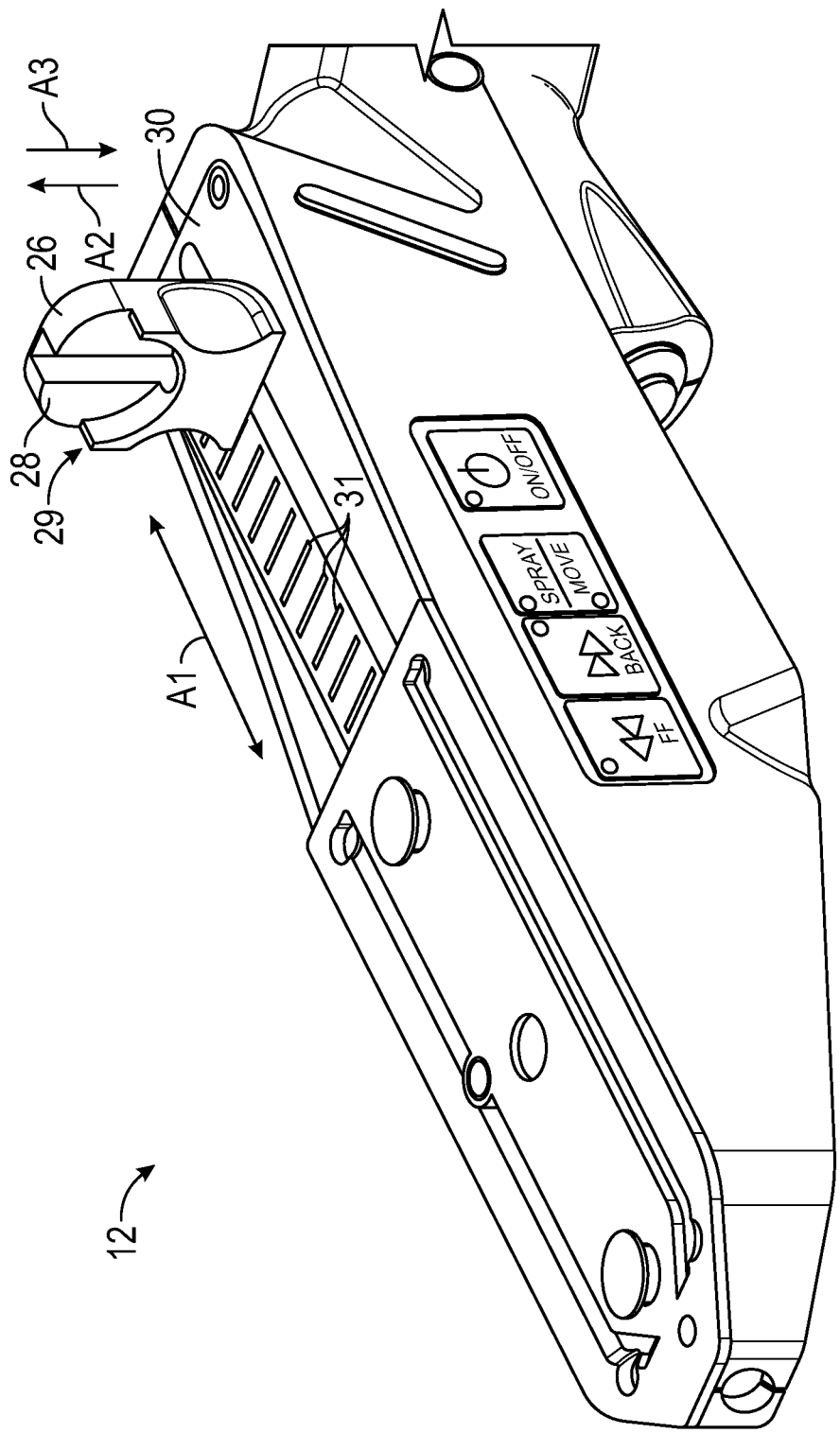
FIG. 2 is a perspective view of an example handheld device, which is a component of the spray deposition system of FIG. 1, in accordance with the present patent application.

The syringe 16 can include a lip 17 and a plunger 24 configured to push the treatment solution 18 through the syringe 16 and out the needle 20. The plunger 24 can be releasably connected to a movable slide 26 on the handheld device 12. As shown in FIG. 2, the movable slide 26 can include a pusher 28 configured to directly contact a tip or flange 25 at an end of the plunger 24. The pusher 28 can be configured to include a recess 29 sized and shaped to receive the tip or flange 25 of the plunger 24. The movable slide 26 can move back and forth on a first top surface 30 of the handheld device 12 in a direction indicated by arrow A1 in FIG. 2. As the slide 26 moves forward, contact between the pusher 28 and the plunger 24, can cause the plunger 24 to also move forward, thus pushing the treatment solution 18 from the syringe 16 and through the end of needle 20. Operation of the movable slide 26 is described further below in reference to FIG. 15. The first top surface 30 can include a plurality of volume markers 31 which can indicate a volume of solution 18 delivered from the syringe 16. In an example, the first top surface 30 can include ten markers 31, each marker corresponding to an increment between 1 and 10 mL. In an example, the first top surface 30 can include a plate with the volume markers 31 formed therein.

The syringe attachment device 14 can include components to support delivery of air through the tubing 22, and such components can include an airflow indicator 32 and an air filter 34, each of which can be in fluid flow with the tubing 22 such that air flowing through the tubing 22 can pass through the air flow indicator 32 and then through the air filter 34, prior to being discharged from the tubing 22. The airflow indicator 32 can include a rotatable element, that if rotating indicates that an air flow through the tubing 22 is occurring. An inlet end of the tubing 22, located opposite to the discharge end, and not shown in the figures, can be connected to an air supply source, such as an air wall outlet in an operating room.

In an example, the air filter 34 can be a Luer-lock air filter with a 0.2 μm pore size for air filtration. In an example, the syringe 16 can be a Luer-lock syringe with Luer-Lock Tip. In an example, the syringe can be a 10 mL syringe.

The handheld device 12 can include a handle portion 36 such that the spray deposition system 10 can be easily gripped by a user of the system 10. The handle portion 36 can include a trigger switch 38, which can actuate a motor inside the handheld device 12 for the spray operation. The handle portion 36 can also include a battery compartment 39 for housing a battery used to supply power for the spray deposition system 10. With the inclusion of a battery, the system 10 can operate without a power unit and power cable.

Figure 7:
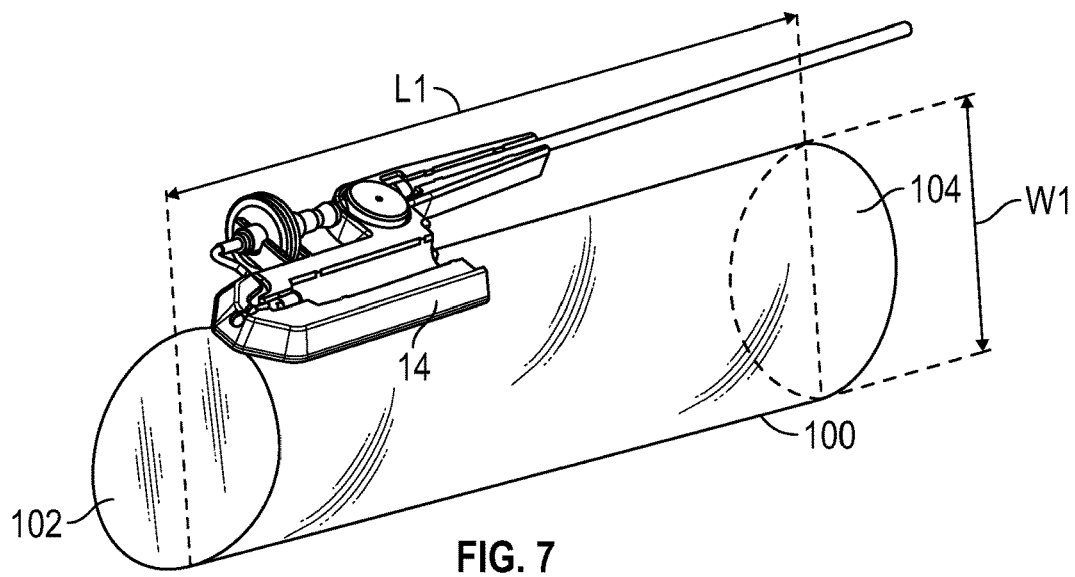
FIG. 7 is a perspective view of the syringe attachment device of FIGS. 3-5 with a cover attached thereto, in accordance with the present patent application.

The handheld device 12 can include a marker 40, which can be used when the spray deposition system 10 includes a sterile cover (see FIG. 7). An opposing side of the handheld device 12 (not shown) can include a corresponding marker in a similar position on the handheld device 12. The marker 40 can be used to aid in alignment with the cover over the handheld device 12, as described further below. It is recognized that more or less markers can be used on the handheld device 12 to aid in alignment of the device 12 with the sterile cover 100.

The handheld device 12 can include a control panel 41 for controlling operation of the spray deposition system 10. The control panel 41 can include a plurality of buttons for operating the handheld device 12. In an example, the control panel 41 can include an on/off button 42. A light 43 on the ON/OFF button 42 can be lit when the system 10 is turned on. A SPRAY/MOVE button 44 can indicate the operational mode of the system 10. After the system 10 is turned on, using button 44, a MOVE mode can be activated automatically and a move light 45 can be on, indicating operation in the MOVE mode. The MOVE mode can include forward or backward movement of the movable slide 26 on the top surface 30 via a forward button 47 or back button 49, respectively. When the MOVE mode is on, lights 48 and 50 of the forward and back buttons 47 and 49, respectively, can be yellow. Once one of the buttons 47 or 49 is pressed, the respective light 48 or 50 turns to green to indicate movement of the slide 26 in a forward or back direction on the surface 30.

Once the syringe 16 is secured within the syringe attachment device 14, as described further below, the system 10 can operate in a SPRAY mode. The user can push down the SPRAY/MOVE button 44 to select the SPRAY mode at which point a spray light can be on, indicating operation in the SPRAY mode, and consequently the light 45 can be off. In the SPRAY mode, the user can "spray" the liquid treatment solution 18 from the syringe 16 by pushing and holding down the trigger switch 38.

It is recognized that the control panel 41 can be arranged in a variety of ways and can include more or less buttons and lights relative to what is shown in FIG. 1. It is recognized that different indicators can be used in addition or as an alternative to the specific lights and colors described above in reference to buttons 42, 44, 47 and 49.

In an example, the movable slide 26 can be moved manually on the top surface 30, as an alternative to the electronic movement described above. The movable slide 26 can be pulled upward in a direction indicated by arrow A2 in FIG. 1. Keeping the slide 26 in this upward position, the slide 26 can then move forward or backwards. Once the desired position of the slide 26 is reached, the slide 26 can be released back in the direction indicated by arrow A3 in FIG. 1.

The handheld device 12 can include a LED light 51 at an end of the handheld device 12 to provide light to aid the clinician or other user of the spray deposition system 10. In an example, the LED light 51 can turn on when the spray mode is activated. In an example, the handheld device 12 can include additional lighting elements, such as a side light bar along a side of the handheld device 12 near the syringe attachment device 14.

It is recognized that some components of the spray deposition system 10 can be optional and the spray deposition system 10 can function as described above without all components described herein and shown in the figures. It is recognized that some components of the spray deposition system 10 can be arranged differently, compared to what is shown in FIG. 1.

In some examples, it may be important or necessary that a portion of the spray deposition system 10 be sterile and remain sterile during delivery of the treatment solution 18 from the syringe 16. FIGS. 7-14 illustrate use of a cover, which can be sterile, with a spray deposition system such that sterile and non-sterile components can be used together during delivery of the treatment solution.

Figure 3:
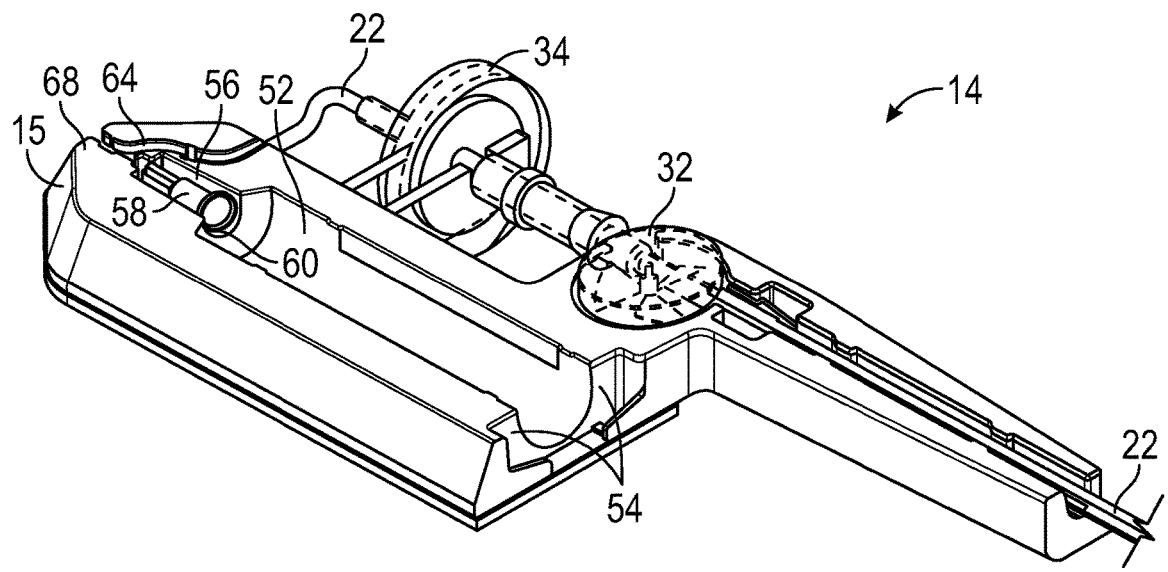
FIG. 3 is a perspective view of an example syringe attachment device, which is a component of the spray deposition system of FIG. 1, in accordance with the present patent application.
Figure 4:
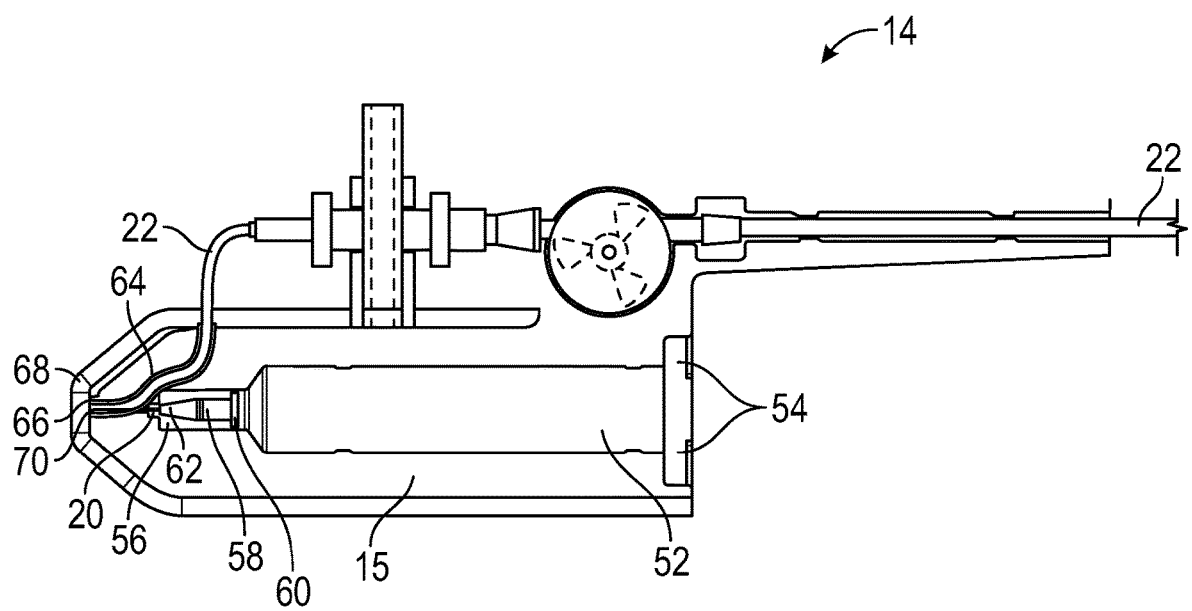
FIG. 4 is a top view of a portion of the syringe attachment device of FIG. 3, in accordance with the present patent application.

FIGS. 3 and 4 show a top portion 15 of the syringe attachment device 14 without the syringe 16. The top portion 15 can include a channel 52 sized and shaped to receive the syringe 16 and a pair of grooves 54 sized and shaped to receive the lip 17 at the end of the syringe 16. As provided further below, the syringe 16 can typically be inserted into the channel 52 after the syringe attachment device 14 is coupled to the handheld device 12. The syringe channel 52 can include a narrowed portion 56 sized and shaped to receive a connector piece 58 that has a first end portion 60 and a second end portion 62. The first end portion 60 can be connected to the syringe 16 when the syringe 16 is inserted into the channel 52. The second end portion 62 can house a portion of the needle 20 such that the needle 20 extends from the connector 58 at a second end portion 62. As shown in FIG. 3, in an example, the connector portion 58 can be tapered such that the first end portion 60 is larger relative to the second end portion 62. In an example, the connector 58 can be a Luer connector and the needle 20 can be a 1.27 cm needle.

As shown in FIG. 4, the tubing 22 can be received within a groove or slot 64 formed in the syringe attachment device 14. A portion of the groove or slot 64 can be curved. A discharge end 66 of the tubing 22 can be near an end portion 68 of the syringe attachment device. The needle 20 extending from the connector piece 58 can pierce through the tubing 22 at a junction 68 of the tubing and the needle 22 can pass through the tubing 22. A delivery end 70 of the needle 22 can be located proximate to the discharge end of the tubing 22. As such, when the spray deposition system 10 is in an assembled position, the treatment solution 18 exiting the syringe 16 can mix with the air passing through the tubing 22 and the treatment solution can become airborne droplets that can be delivered as a fine spray to the targeted area.

The syringe attachment device 14 can be designed such that essentially only the syringe 16 needs to be assembled into the device 14, after the device 14 is attached to the handheld device 12. The tubing 22 can already be attached within the device 14 and the needle 20 can already be in place within the device 14. This design can be safer for the clinician, given prior placement of the needle 20 when the clinician receives the device 14. Moreover, this design can be easier for the clinician since the components within the device 14 are already pre-assembled for the clinician or other user.

Figure 5:
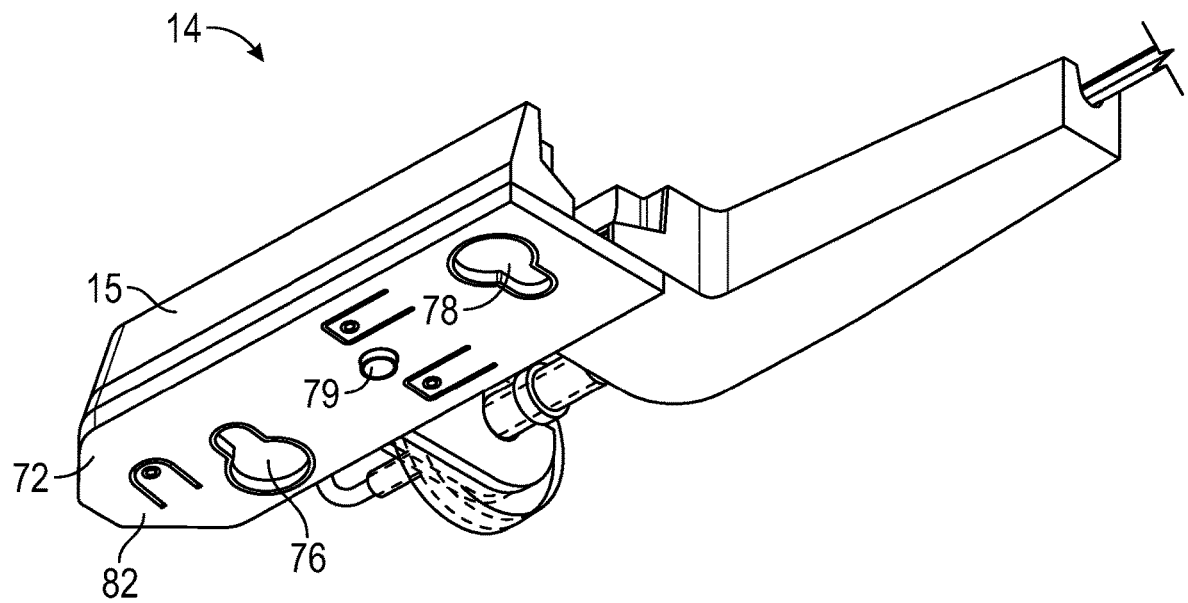
FIG. 5 is a perspective view of a bottom of the syringe attachment device of FIGS. 3 and 4, in accordance with the present patent application.

As shown in FIG. 5, the syringe attachment device 14 can include two parts that can be attached or coupled together. The top portion 15 can be coupled to a bottom plate 72. The bottom plate 72 can also be referred to as a bottom portion of the syringe attachment device 14. In an example, the top portion 15 and the bottom plate 72 can be attached together by way of a snap fit or interference fit. Each of the top portion 15 and the plate 72 can include features that correspond or mate with one another such that the top portion 15 and the plate 72 can be coupled together. (See, for example, FIG. 8.) It is recognized that other methods can be used to attach the top portion 15 to the bottom plate 72. The top portion 15 and the plate 72 can be releasably coupled together such that the top and bottom portions 15 and 72 can be separated after they have been coupled together. In other examples, the bottom plate 72 and the top portion 15 may not be separate pieces and the syringe attachment device can be a one piece design (see, for example, FIG. 13).

Figure 6:
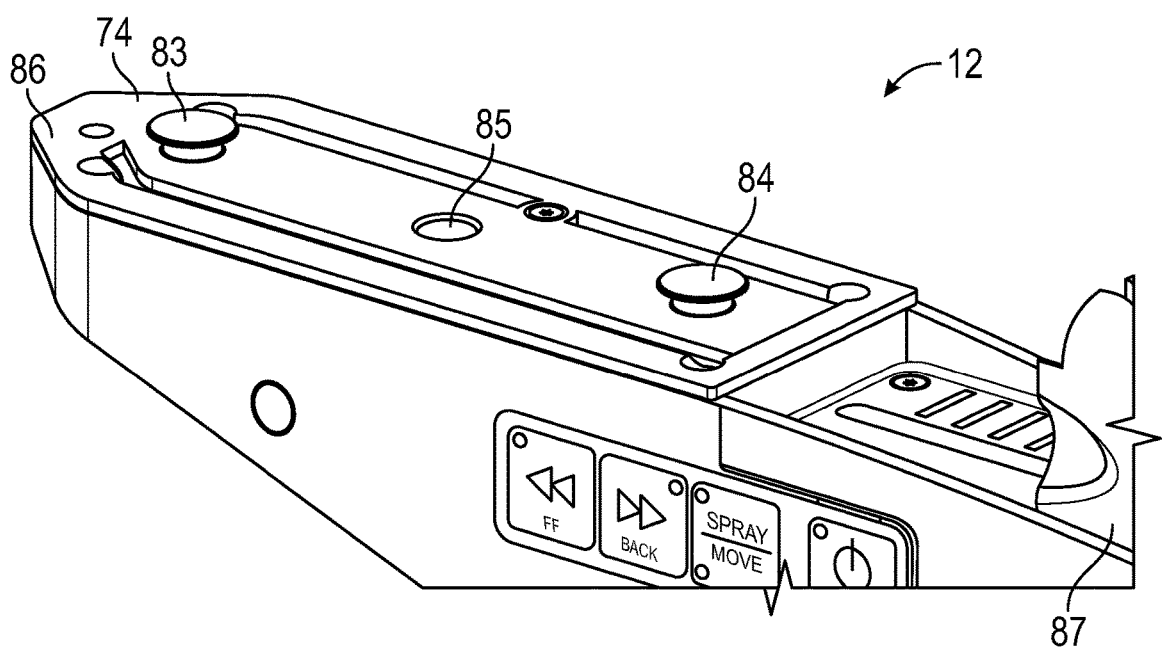
FIG. 6 is a perspective view of the handheld device of FIG. 2, in accordance with the present patent application.

As described above, the syringe attachment device 14 and the handheld device 12 can be coupled together in an assembled position. FIG. 5 illustrates that the bottom plate 72 of the syringe attachment device 14 can include one or more features and FIG. 6 illustrates that a second top surface 74 of the handheld device 12 can include one or more corresponding features for coupling the device 14 to the handheld device 12. In an example, the bottom plate 72 of the device 14 can include a first keyhole 76 and a second keyhole 78, each formed through the bottom plate 72, and a protrusion 79 extending from a bottom surface 82 of the plate 72. In such example, the second top surface 74 of the device 12 can include a first protrusion 83 and a second protrusion 84, each extending from the second top surface 74, corresponding to the first keyhole 76, and the second keyhole 78, respectively, and an aperture 85 formed in the second top surface 74 and corresponding to the protrusion 79. Thus, in the example represented in FIGS. 5 and 6, each of the devices 12 and 14 can have three connecting elements. It is recognized that in other examples, each of the devices 12 and 14 can have more or less connecting elements. It is recognized that the devices 12 and 14 do not have to be coupled together using the specific combination of features shown in FIGS. 5 and 6; other elements or designs can be used in addition to or as an alternative to the features shown in FIGS. 5 and 6.

The syringe attachment device 14 can be coupled to the handheld device 12 by bringing the bottom surface 72 of the device 14, at the end portion 68, in proximity to a first end portion 86 of the device 12 at an angle such that an opposite (second) end portion 87 of the device 14 is at a further distance from the device 14. The device 14 can then be rotated in a clockwise direction until the device 14 engages with the device 12. It is recognized that attachment can vary, depending, for example, on the orientation of the keyholes 76 and 78 in the bottom plate 72 of device 14. After the devices 12 and 14 are coupled together, the syringe 16 can be assembled in place and the spray deposition system 10 (see FIG. 1) can be ready for use. Securing the syringe 16 in the device 14 is described below in reference to FIG. 11.

The handheld device 12 and the syringe attachment device 14 can be designed such that the devices 12 and 14 can be releasably coupled to each other. Allowing for separation of the devices 12 and 14, once attached together, can be beneficial if, for example, one or both of the devices 12 and 14 is reusable, as described further below.

One or more of the components of the devices 12 and 14 can be vacuum casted. In addition or as an alternative to vacuum casting, three dimensional (3D) printing can be used for forming all or parts of the devices 12 and 14. The materials for forming the devices 12 and 14 can be biocompatible and medical grade. The spray deposition system 10 can include an electronically controlled apparatus used as a medical device to operate the spraying through a sterilizable spray head. The system 10 can enable a distribution of cells using about 0.5 to about 60±20 milliliter sterile cell suspension through a spray head. In an example, the syringe 16 can be a medical grade disposable sterilizable syringe, including about 0.5 to about 60 milliliter sterile Luer-lock syringes, or other secure syringes, and the syringe 16 can transfer the cell suspension (the treatment solution 18) from the system 10 to the subject or patient.

The system 10 can be operated by producing a gas flow, for example air from a compressor, to engage the spray head, or forcing the cell suspension pump driven through the nozzle, for example by motor operated pushing of the syringe 16 containing the cell suspension (the treatment solution 18). In an example, the system 10 can provide continuous force application over a range of about 0.5 to about 10±1.0 minutes for one or more shots, and generate suspension drops containing cells in the range of about 30 to about 500±200 millimeters. The system 10 can provide means to measure and control parameters such as flow, pressure, and/or temperature.

The system 10 can transfer the cell suspension from a medical grade sterilizable container to the sterilizable spray head via a disposable filter capable of separating large cellular congregates from a cellular suspension. Any filter capable of separating excessively large cellular congregates from the suspension can be used. The filter can exhibit a cut off of about 5 cells to about 100 cells, preferably about 20 to about 60 cells and most preferably about 40 cells. The filter can cut off outside of these ranges, however noting that if the filter cuts off smaller cell aggregates, cells can be lost for the patient, and if the filter cuts off larger cell aggregates, the system can clot.

An air flow rate of air delivered through the tubing 22 can be sufficient to ensure adequate spray distribution of the cells from the treatment solution 18. In an example, the air flow rate can be from about 3 to about 7 liters per minute, from about 3 to about 5 liters per minute, and from about 3 to about 3.5 liters per minute. The travel speed of the syringe plunger 24 can control a rate at which the cells from the treatment solution 18 exit the syringe 16. In an example, the travel speed can be from about 1 to about 3.5 milliliters per minute. In an example, the travel speed can be about 2.5 milliliters per minute. In an example, the travel speed of the plunger 24 can be a preset of the spray deposition system.

The spray deposition system 10 can be used for delivering various types of treatment solutions to a patient, an example of which is autologous skin cells. It can be beneficial or critical that at least a portion of the spray deposition system 10 is sterile during delivery of the treatment solution 18. However, it can be difficult to sterilize all of the spray deposition system 10. FIGS. 7-14 illustrate examples of the spray deposition system 10 having a cover integrated into the design of the spray deposition system 10 to facilitate easier and faster preparation of the spray deposition system 10 for the clinician and other users. As described below, the cover can be directly affixed to the syringe attachment device 14. In an example, the cover can be sterile and the use of the sterile cover in combination with the system 10 can facilitate handling an unsterile device (for example, the handheld device 12) in a sterile manner during use of the system 10 for delivering the treatment solution 18.

Figure 8:
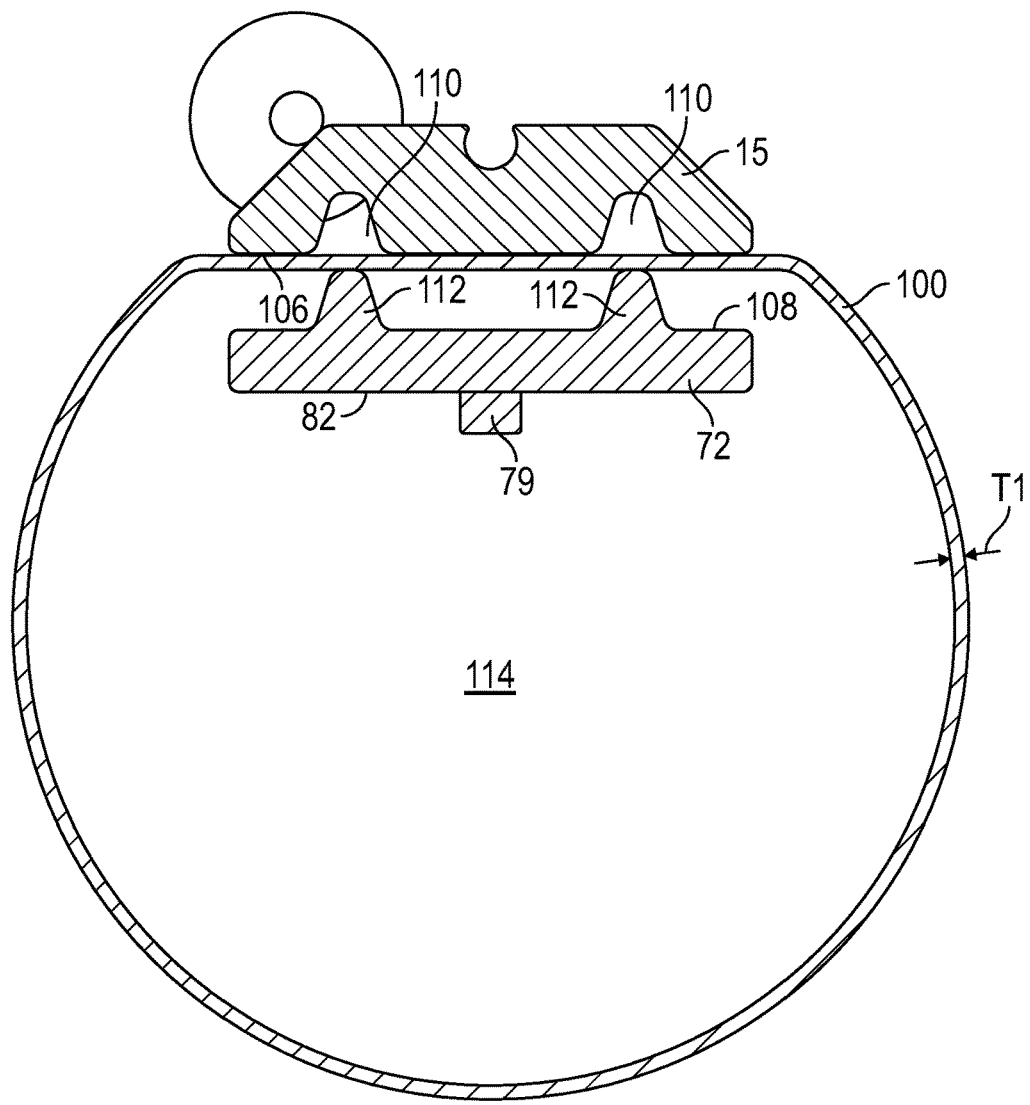
FIG. 8 is a cross-sectional view of the syringe attachment device and cover of FIG. 7, in accordance with the present patent application.

FIGS. 7 and 8 illustrate the syringe attachment device 14, as described above, in combination with a cover 100 attached to the syringe attachment device 14. The cover 100 is described herein as a sterile cover 100; however, it is recognized that the cover 100 may be non-sterile. In an example, the sterile cover 100 can have a generally tubular shape and can be closed at a first end 102 and open at a second end 104. It is recognized that the sterile cover 100 does not have to have a tubular shape and can have other cross-sectional shapes, such as, for example, rectangular, triangular, etc. The first end 102 of the sterile cover 100 can be in proximity to the end portion 68 of the syringe attachment device 14 in an attached position. As described below and shown in FIGS. 9-12, the sterile cover 100 can be sized and shaped such that the handheld device 12 (not shown in FIGS. 7 and 8) can be inserted into the sterile cover 100 through the second end 104 and enclosed within the sterile cover 100.

The sterile cover 100 can be attached to the syringe attachment device 14 using any known connection means suitable for medical components. In an example in which the syringe attachment device 14 includes the top portion 15 and the bottom plate 72, the sterile cover 100 can be attached to the syringe attachment device 14 by inserting the sterile cover 100 between the top portion 15 and the bottom plate 72. FIG. 8 is a cross-sectional view of the syringe attachment device 14 and the sterile cover 100, during an assembly of the sterile cover 100 to the syringe attachment device 14. The sterile cover 100 can be placed between a bottom 106 of the top portion 15 and a top 108 of the bottom plate 72, before the top portion 15 and bottom plate 72 are coupled together. The sterile cover 100 can be aligned with the syringe attachment device 14 such that the closed end 102 of the sterile cover 100 is aligned with the end portion 68 of the syringe attachment device.

Each of the top portion 15 and bottom plate 72 can include corresponding features to enable removable coupling of the two parts together. In an example, the top portion 15 can include a pair of recesses 110 formed in the bottom 106 that can correspond to a pair of protrusions 112 extending from a top 108 of the bottom plate 72. The protrusions 112 can be configured to snap fit into the recesses 110. Although only one pair of recesses and protrusions is shown in FIG. 8 (since it is a cross-sectional view), it is recognized that the top portion 15 and the bottom plate 72 can include more than one pair of recesses and protrusions, respectively. Moreover, it is recognized that other features can be used to removably couple the top portion 15 and the bottom plate 72. In other examples, the top portion 15 and the bottom plate 72 can be irreversibly coupled to one another after the sterile cover 100 is inserted there between.

Once the top portion 15 and the bottom plate 72 are coupled together, the bottom surface 82 of the bottom plate 72 can be contained within an interior 114 of the sterile cover 100. As described below and illustrated in FIGS. 9 and 10, the syringe attachment device 14 can then be removably coupled to the handheld device 12.

Although not included in FIG. 7, the sterile cover 100 can include one or more markers on an exterior or an interior of the sterile cover 100, such one or more markers can be used to aid in placement of the handheld device 12 inside the sterile cover 100 or insertion of the syringe 16 (see FIG. 1) in the syringe attachment device 14 after the devices 12 and 14 are coupled together. Such one or more markers can be part of the material used in forming the sterile cover 100 or another material attached to the exterior or interior of the sterile cover 100. In an example, the sterile cover 100 can include one marker (see marker 116 of FIGS. 9-12) extending around all or a portion of a circumference on the exterior of the sterile cover 100.

The sterile cover 100 can be sized and shaped to cover the handheld device 12, and in some cases, have extra length such that the sterile cover 100 can be tied off near the second end 104. In an example, the sterile cover 100 can have a length L1 ranging from about 1 centimeter (cm) to about 500 cm, from about 10 cm to about 200 cm, from about 20 cm to about 100 cm, from about 45 to about 75, and from about 55 to about 65 cm. In an example, the sterile cover 100 can having a width W1 ranging from about 1 cm to about 500 cm, from about 10 cm to about 200 cm, from about 10 cm to about 50 cm, from about 12 cm to about 25 cm, and from about 15 cm to about 20 cm. In an example, the length L1 can be greater than the width W1. In an example, the length L1 can be three or more times greater than the width W1. In an example in which the sterile cover 100 is generally tubular shaped, the width W1 can generally be equivalent to a diameter of the sterile cover 100.

It is recognized that the dimensions of the sterile cover 100 can vary. The length L1 and width W1 can be larger or smaller depending on a size and shape of the syringe attachment device 14 and the handheld device 12. It is recognized that the syringe attachment device 14 and the handheld device 12 do not have to have the exact shape and design as shown in the figures herein.

In an example, the sterile cover 100 can have a thickness T1 ranging from about 0.01 millimeter (mm) to about 2 mm, from about 0.02 mm to about 1 mm, from about 0.05 mm to about 0.8 mm, and from about 0.1 mm to about 0.5 mm. The sterile cover 100 can be designed such that it is thin enough to fit between the top portion 15 and the bottom portion 72 of the syringe attachment device 14 (see FIG. 8) and between the tip 25 of the syringe plunger 24 and the pusher 28 of the movable slide 26 (see FIG. 11). The sterile cover 100 can be designed such that it is flexible and thin such that the clinician or user can grasp or manipulate the handheld device 12 when the handheld device 12 is contained within the sterile cover 100 and the operating elements of the handheld device 12 can be operated without difficulty. The handheld device 12 can have a close fit or a loose fit with the cover 100.

The sterile cover 100 can be formed from any material or materials suitable for medical applications and capable of having the properties described above. In an example, the sterile cover 100 can be formed from one or more materials including, but not limited to, polyurethane, polyacrylate, polyvinylchloride, polyethylene, polylactide, cellulose acetate, silicone, or combinations thereof. In an example, the sterile cover 100 can be formed of one or more materials, such as, for example, polyethylene and polyvinylchloride, that can have self-adhesive properties, such that the sterile cover 100 itself can be used to close an open end of the sterile cover 100 once the handheld device 12 is inserted therein. In an example, the sterile cover 100 can be transparent, translucent or opaque, or at least partially transparent, translucent or opaque, which can permit the clinician or user to see the handheld device 12, and the components thereof, when the handheld device 12 is contained within the sterile cover 100.

Figure 9:
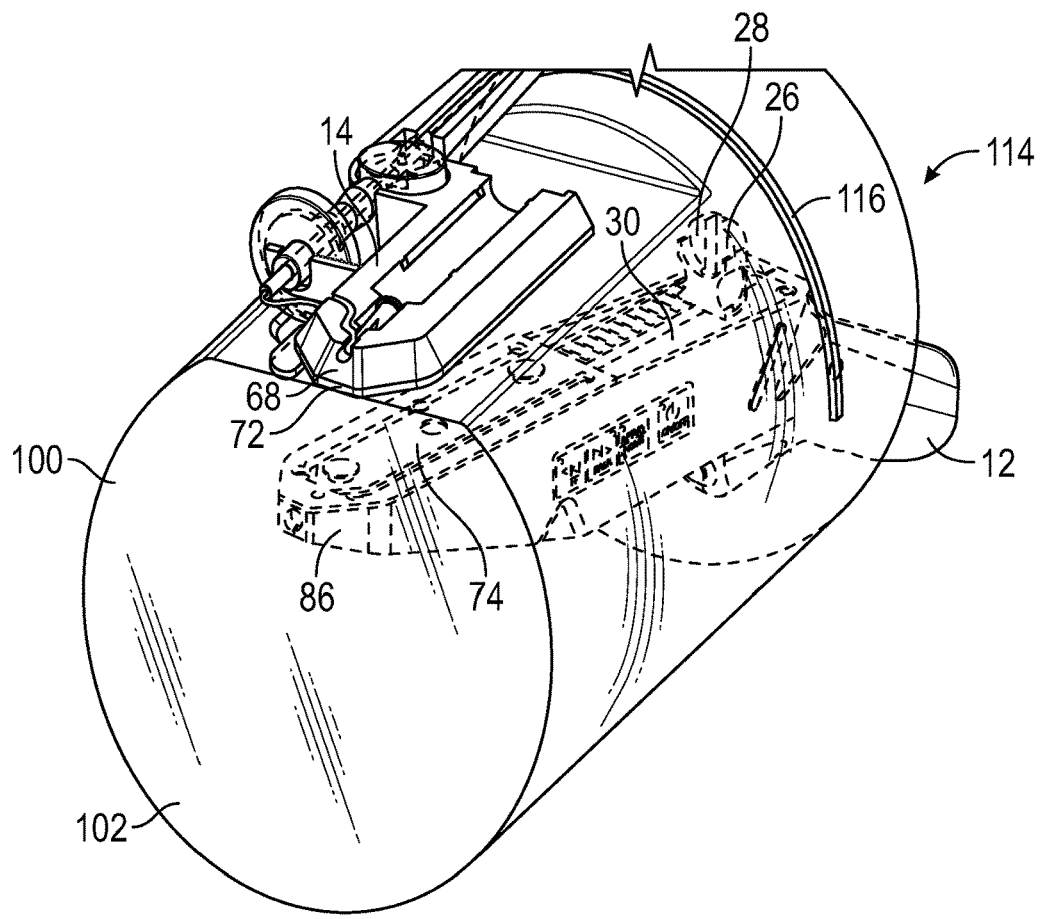
FIGS. 9-11 are perspective views of the spray deposition system having a cover, during assembly of the system, in accordance with the present patent application.

FIGS. 9-12 illustrate assembly of the spray deposition system 10 in a design in which the spray deposition system 10 includes the sterile cover 100. It is recognized that the spray deposition system 10 as shown in FIG. 1 can be used without a sterile cover, or different means can be used to provide appropriate sterility of the spray deposition system 10. As described above in reference to FIGS. 7 and 8, the syringe attachment device 14 and the sterile cover 100 can be pre-assembled together, and in an example, the clinician or user can receive the device 14 and the sterile cover 100 in such pre-assembled form. As shown in FIG. 9, the user or clinician can insert the handheld device 12 into the interior 114 of the sterile cover 100 with the first end portion 86. The handheld device 12 can be inserted into the interior 114 until the first end portion 86 of the handheld device 12 is generally at the closed end 102 of the sterile cover 100. The sterile cover 100 can include one or more markers that can help with aligning the handheld device 12 inside the sterile cover 100. In an example, the sterile cover 100 can include marker 116, described further below.

Figure 10:
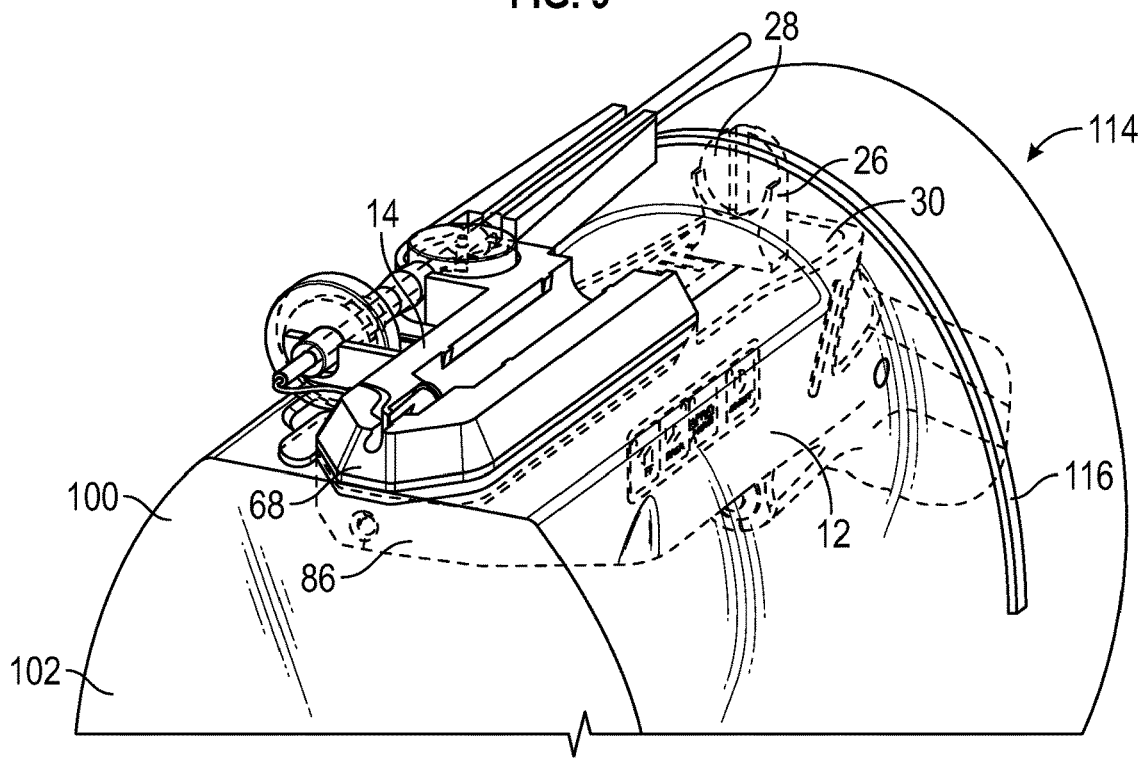

The bottom surface 82 of the plate 72 of the device 14 at the end portion 68 can be placed on the second top surface 74 of the device 12 at the first end portion 86, with the device 14 at an angle relative to the device 12. Then, as described above in reference to FIGS. 5 and 6, the device 14 can be rotated in a clockwise direction, relative to the device 12, until the device 14 is properly in engagement with the device 12 and the devices 12 and 14 can be in parallel with one another, as illustrated in FIG. 10.

The movable slide 26, extending from the first top surface 30 of the handheld device 12, can cause the sterile cover 100 to lift up at a region of the sterile cover 100 that is in alignment with the movable slide 26. Because the sterile cover 100 can be thin and flexible, the sterile cover 100 can undergo this type of deformation or movement caused by the movable slide 26. The marker 116 can be used to ensure proper placement of the handheld device 12 relative to the sterile cover 100. In an example, the marker 116 can extend around at least a portion of the circumference of the cover 100 at a location designed to coincide with the location of the pusher 28 of the movable slide 26, when the handheld device 12 is generally properly aligned with the sterile cover 100. It is recognized that additional or alternative markers can be used. The marker 116 can be on an interior or an exterior of the sterile cover 100.

Figure 11:
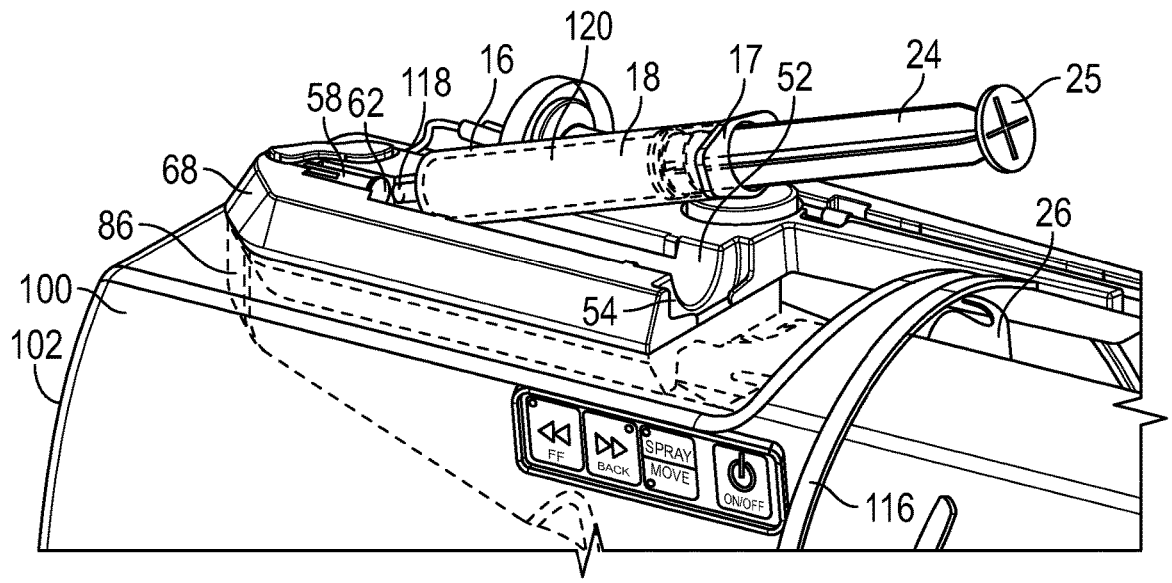

As shown in FIG. 11, the syringe 16, containing the treatment solution 18, can be secured within the channel 52 of the syringe attachment device 14. An end 118 of the syringe 16 can be inserted into the second end portion 62 of the connector 58, a body 120 of the syringe can be inserted into the syringe channel 52 and the lip 17 of the syringe 16 can be inserted into the grooves 54 adjacent the channel 52. At this point, the tip 25 of the plunger 24 may not have contact with the pusher 28 of the movable slide 26 on the handheld device. In that case, the clinician or user can move the movable slide 26 in a direction toward the end portion 68 of the device 14 until the pusher 28 is in contact with the tip 25 of the plunger 24. In an example, when the MOVE light 45 of the spray/move button 44 (see FIG. 1) is on, the movable slide 26 can be advanced in the direction toward the end portion 68 using the forward button 47 of the control panel 41 on the handheld device 12. (The movable slide 26 can also be manually moved.) When the pusher 28 comes into contact with the tip 25 of the plunger 24, the sterile cover 100 can be clamped in between the plunger 24 and the slide 26. In an example, the marker 116 can designate the position on the sterile cover 100 that should be inserted between the plunger 24 and the slide 26. Even though the movable slide 26 is contained inside the sterile cover 100 and the syringe 16 is outside the sterile cover 100, the movable slide 26 can be advanced, manually or electronically, to eject the treatment solution 18 from the syringe 16.

Figure 12:
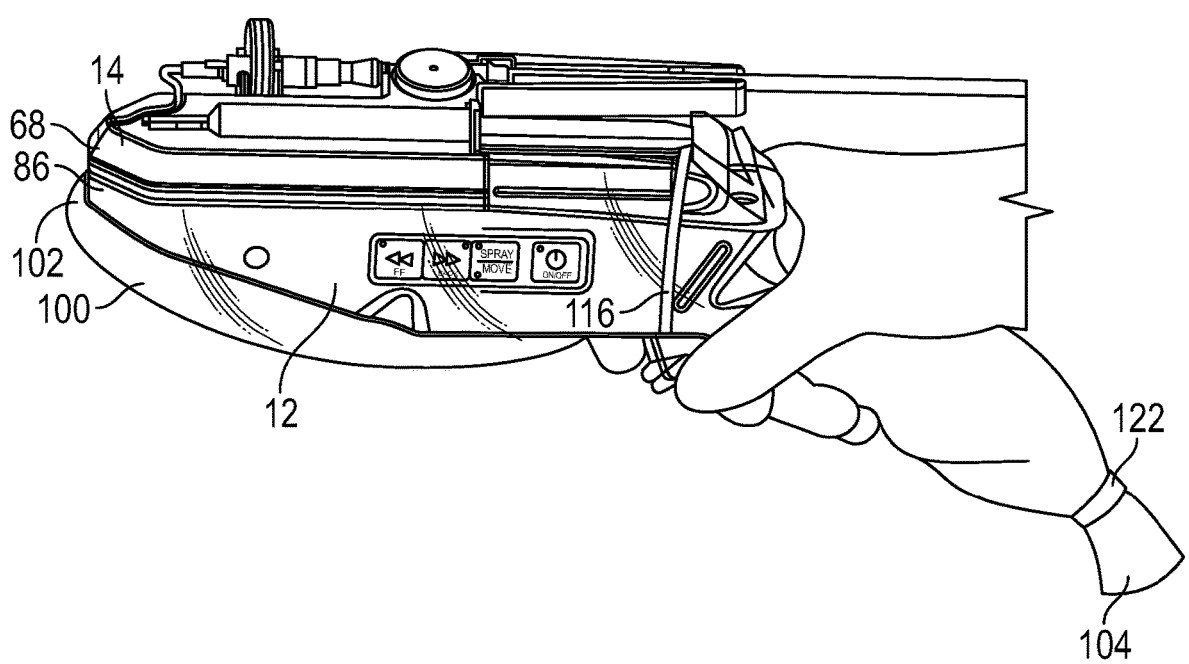
FIG. 12 is a side view of the spray deposition system, in an assembled position, in accordance with the present patent application.

After the syringe 16 is in place, the sterile cover 100 can be closed off near the second end 104 to essentially seal the sterile cover 100. In an example, as shown in FIG. 12, a rubber band 122 can be wrapped around the sterile cover 100 near the second end 104. The rubber band 122 can be used to create an essentially air-tight connection or seal such that any contaminants inside the sterile cover 100 cannot escape interior 114 of the sterile cover 100 and pass from the handheld device 12 through the cover 100. Any contaminants can thus be contained within the interior 114 of the sterile cover 100.

As an alternative to or addition to the rubber band 122, one or more other components can be used to facilitate closing of the sterile cover 100 around the handheld device 12. In an example, the one or more materials used to form the sterile cover 100 can include an adhesive or a portion of the one or more materials for forming the sterile cover 100 can have adhesive properties. In an example, the system 10 does not include an additional component for closing off the open end 104 of the sterile cover 100, but rather the adhesive on the sterile cover 100 or the adhesive properties of the cover 100 itself facilitate closing off of the sterile cover 100 at the open end 104 after the handheld device 12 is enclosed within the sterile cover 100.

In an example, after closing off the sterile cover 100, the user can adjust the handheld device 12 and the sterile cover 100. Such adjustment can include holding the handheld device 12 near the rubber band 122 with a first hand and grasping the sterile cover 100 with the other hand, on the other side of the rubber band 122 opposite the second end 104. The cover 100 can be moved with the first hand towards the first end portion 86 of device 12. The sterile cover 100 can include a second marker (not shown) located after the marker 116 on the sterile cover 100 closer to the second end 104. Once the second marker is aligned with the marker 40 on the handheld device 12, the user can stop moving the sterile cover 100. In an example, the second marker can be located about 7.5 cm to about 9.5 cm from the marker 116.

After the sterile cover 100 is sealed, the inlet end of the tubing 22 can be connected to the air supply.

In summary, the handheld device 12, which in an example can be an unsterile portion of the system 10, can be isolated from a portion of the syringe attachment device 14, which is sterile, in order that such sterile portion of the syringe attachment device 14 can be protected from possible contamination and can remain sterile during use of the system 10. The sterile cover 100 can protect the syringe attachment device 14 from possible contaminants that can compromise the sterility of the syringe attachment device 14. The handheld device 12, which can be considered the main equipment of the system 10, can be used in a surgical operating environment in combination with the sterile cover 100, without sterilization of the handheld device 12. The handheld device 12 can be reusable, and subsequent use of the handheld device 12 does not require sterilization if a new sterile cover is used (with a new syringe attachment device). Benefits of the systems and methods described herein can include time efficiency, avoidance of energy usage or chemicals for the sterilization of the handheld device 12, and avoidance of potential damage to the handheld device 12. Consequently the systems and methods can be more economical and ecological compared to systems and methods requiring sterilization of the handheld device 12.

In an example, the cover 100 is sterile. In an example, the sterile cover 100 can be used in combination with a sterile treatment solution 18 and the syringe 16 can be sterile. It can be beneficial to maintain the sterility of the treatment solution 18. The syringe 16 can be secured to the syringe attachment device 14, which can also be sterile. When the treatment solution 18 is prepared (see below), efforts can be taken to disinfect or clean the skin area prior. Similarly, when the cells in the treatment solution 18 are sprayed on the skin of the subject, the skin to be sprayed can be disinfected or cleaned beforehand.

In an example, the cover 100 does not have to be sterile, even though it is referred to herein as the "sterile" cover 100. In an example, a non-sterile form of the cover 100 can be used when one or more components of the syringe attachment device 14 and the handheld device 12 are clean but not necessarily sterile. This can include, but is not limited to, applications in which it may not be possible or necessary to have a sterile environment, such as field applications, training, veterinary applications or emergency uses.

In an example, the handheld device 12 can be reused, and the syringe attachment device 14 can be disposed of after the treatment solution 18 is applied to the patient. Even though the handheld device 12 does not need to be sterilized before or after each use, it is recognized that the handheld device 12 can be cleaned before or after each use. In an example, select cleaning solutions can be used to clean a surface of the handheld device 12. Such clean solutions can include, for example, isopropyl alcohol, soapy water, diluted chlorine bleach, ammonia based cleaners, glutaraldehyde-based cleaners and hydrogen peroxide. Care can be taken not to get fluids inside the device 12.

As described earlier, the spray deposition system may or may not include a sterile cover, and the spray deposition system may or may not be sterile. In an example in which the sterile cover is excluded from the spray deposition system, one or more components of the spray deposition system can be non-sterile prior to use of the spray deposition system.

In an example in which one or more components of the spray deposition system are sterile, sterilization can be achieved using known sterilization techniques, including, for example, gas, radiation or an autoclave which can use high heat and steam. In an example, the syringe attachment device 14 can be sterilized using ethylene oxide.

The sterile cover 100 is shown in FIG. 7 having a generally tubular shape and an elongated design in which the length L1 is significantly greater than the width W1. In an example, the sterile cover 100 can be provided to the user as it is shown in FIG. 7. In an example, the sterile cover 100 can be folded up and provided to the user in a folded configuration. In an example, the sterile cover 100 can be folded by taking the second end 104 and placing the second end 104 on top of the sterile cover 100 at some portion between the first and second ends 102 and 104. Additional folds can be completed in a likewise manner. The sterile cover 100 can also be folded by taking the second end 104 and placing it on an underside of the sterile cover 100 at some portion between the first and second ends 102 and 104.

In an example, the sterile cover 100 can be folded by taking the second end 104 and pulling the second end 104 toward the first end 102 by exposing the inside of the sterile cover 100 and pulling it back as the second end 104 is pulled toward the first end 102. The second end 104 can be pulled toward the first end 102 so far as needed or desired. The newly created open end of the sterile cover 100 can then be turned back again one or more times as desired.

In either of the examples described above, the sterile cover 100 can be supplied to the clinician or user in a folded configuration. The sterile cover 100 can be unfolded to its full length L1 before or after the handheld device 12 is inserted into the interior 114 of the sterile cover 100.

Figure 13:
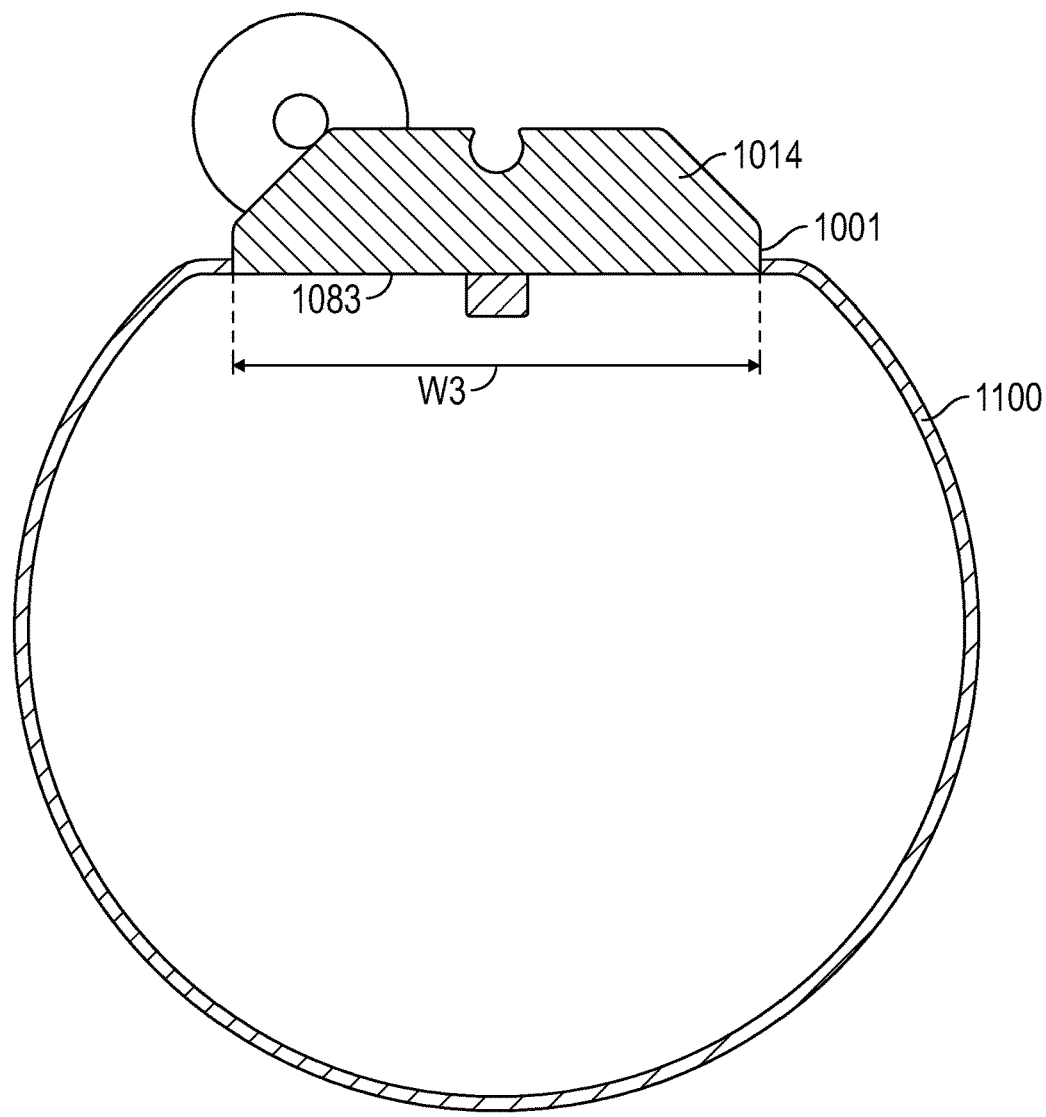
FIG. 13 is a cross-sectional view of an example syringe attachment device and cover, in accordance with the present patent application.

FIG. 13 illustrates an example syringe attachment device 1014 and cover 1100. Instead of the cover 1100 being inserted between parts of the syringe attachment device 1014 (as shown in FIG. 8), the cover 1100 can be attached to an outer surface 1001 of the syringe attachment device 1014. In an example, the cover 1100 can be bonded with an adhesive to the outer surface 1001 around a perimeter of the syringe attachment device 1014. In an example, the cover 1100 can be sterile. In an example, the cover 1100 can be non-sterile or unsterile.

Figure 14:
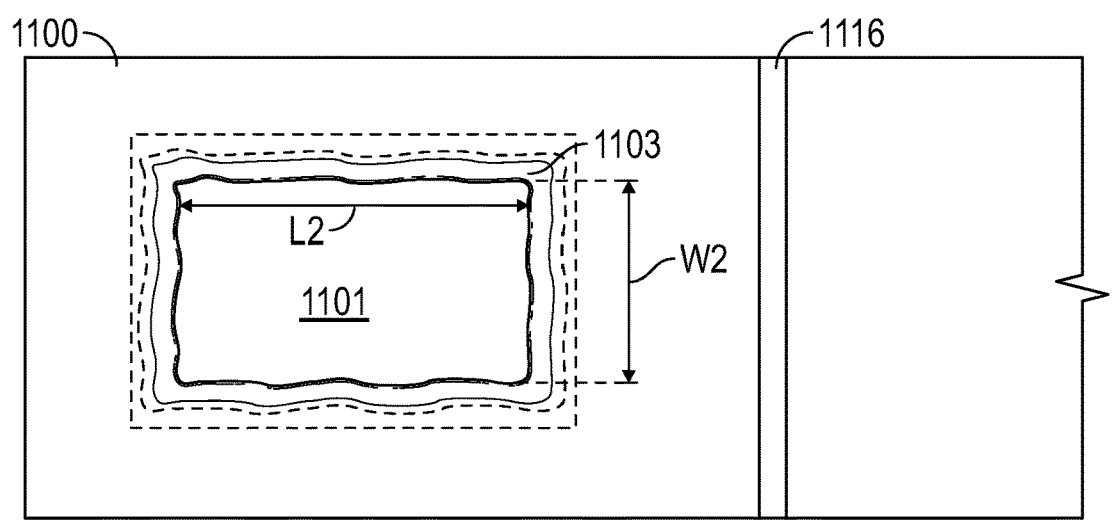
FIG. 14 is a top view of an example cover for use in a spray deposition system, in accordance with the present patent application.

FIG. 14 illustrates the cover 1100 of FIG. 13 before it is attached to the syringe attachment device 1014. The cover 1100 can include an opening 1101 formed through a top portion of the cover 1100 and sized and shaped to generally correspond to dimensions of an outer perimeter of the syringe attachment device 1014. The opening 1101 can have a width W2 generally corresponding to a width W3 of the syringe attachment device 1014. The cover 1101 can include an adhesive 1103 on the top portion of the cover 1100 around the opening 1101. The adhesive 1103 can be configured to attach the cover 1100 to the outer surface 1001 of the syringe attachment device 1014. In an example, the adhesive 1103 can be a biocompatible and medical grade material suitable for bonding the cover 1100 to the syringe attachment device 1014.

The cover 1100 can include a marker 1116 which can be similar to the marker 116 described above. In an example, the marker 1116 can be formed on an exterior of the cover 1100. It is recognized that the cover 1100 can include additional markers for ensuring proper alignment of the syringe attachment device 1014 and the cover 1100 to the handheld device.

In another example, instead of adhesively bonding the cover 1100 to the syringe attachment device 1014, the cover 1100 can be welded to the outer surface 1001 around a perimeter of the syringe attachment device 1014.

As shown in FIG. 13, the syringe attachment device 1014 can be a one piece design rather than having two pieces (top portion 15 and bottom plate 72). A bottom surface 1083 of the syringe attachment device 1014 can include similar features, as described above for the bottom plate 72 (see FIG. 5) such that the syringe attachment device 1014 can engage with a handheld device in a similar manner as described above under FIGS. 5 and 6.

In any of the designs provided above, the syringe attachment device 14 or 1014 and the cover 100 or 1100 can be pre-assembled, under sterile conditions or alternatively under clean but not necessarily sterile conditions, and provided as such to the clinician or other user. The syringe attachment device 14 or 1014 can be provided to the clinician with the attachments and supporting components in place, with the exception of the syringe 16, such that the clinician can easily assemble the spray deposition system as provided above in reference to FIGS. 9-12.

In an example, instead of a tubular configuration having a closed end, a scover in the form of a flat sheet can be used. Such flat sheet can be attached to the syringe attachment device 14 using any of the methods described above, including inserting the sheet between two portions of the device 14 or attaching the flat sheet to the device 14 through bonding or welding. The flat sheet can be sized and shaped to adequately cover the handheld device 12 when the devices 12 and 14 are coupled together and have enough material leftover to adequately tie off or otherwise seal the flat sheet, with the handheld device 12 contained within the interior. In an example, the flat sheet can be provided to the user in a folded configuration, and the flat sheet can be unfolded around the handheld device 12.

Figure 15:
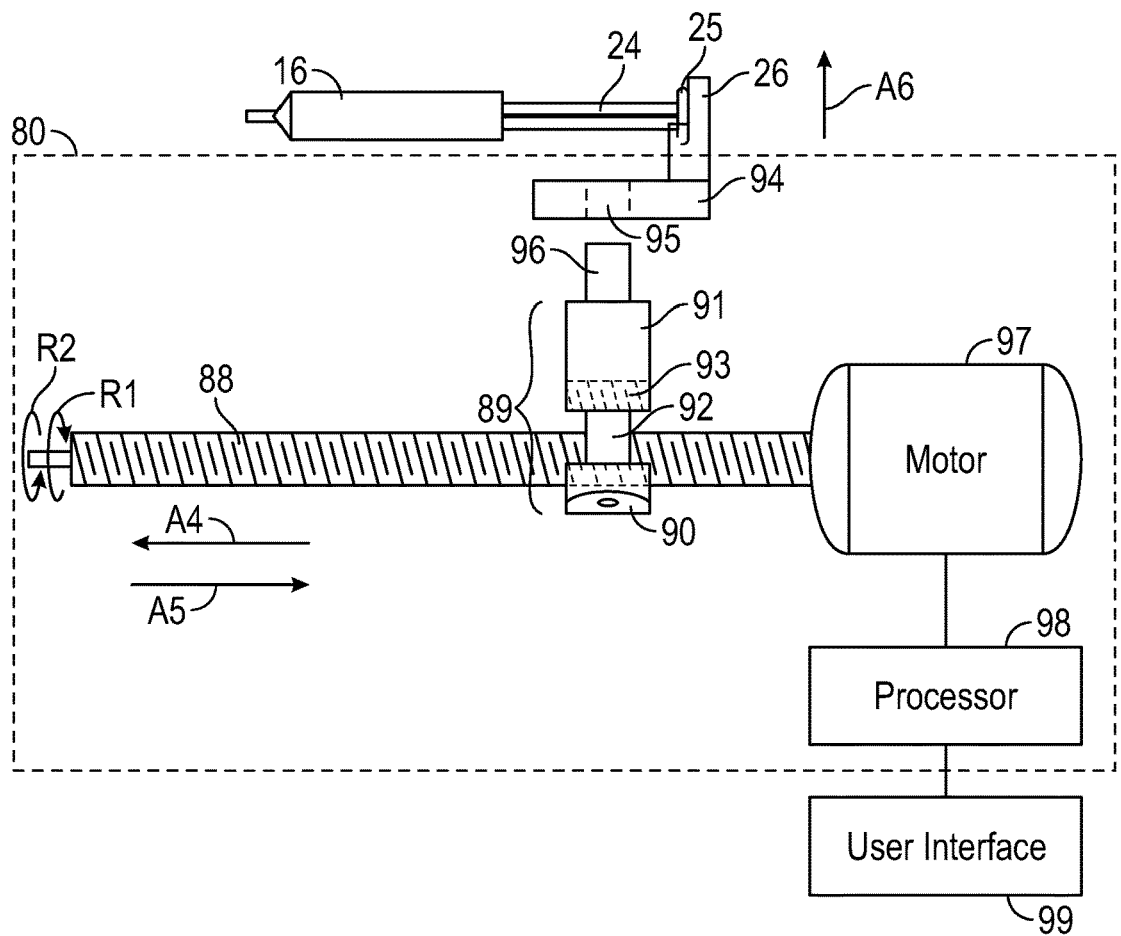
FIG. 15 is a schematic of a portion of the spray deposition system of FIG. 1 to illustrate a gearing mechanism for moving a component of the spray deposition system, in accordance with the present patent application.

FIG. 15 illustrates an example control mechanism for moving the movable slide 26 forward and backward on the handheld device 12, in order to spray the treatment solution 18 from the syringe 16. As described above, the movable slide 26 can be moved either manually or electronically, using a control system 80 that can be part of the spray deposition system 10.

The control system 80 can include a threaded shaft 88 that can be generally oriented in parallel with the syringe 16 and the plunger 24. The threaded shaft 88 can be rotated in a direction indicated by arrow R1 or a direction indicated by arrow R2, both in FIG. 15, using a motor 97. A coupler 89, which can ride on the shaft 88, can move in a forward direction indicated by arrow A4 or a backward direction indicated by arrow A5, depending on the direction of rotation R1 or R2 of the shaft 88.

The coupler 89 can include a lower saddle 90 and an upper saddle 91. The saddles 90 and 91 can be connected to one another by an elastic element 92. In an example, the elastic element 92 can include one or more springs between the lower and upper saddles 90 and 91. The lower saddle 90 can include a smooth half-bore such that the lower saddle 90 is able to move in the direction of arrows A4 and A5 on the threaded shaft 88. The upper saddle 91 can include a threaded half-bore 93 that can engage the threaded shaft 88 when the lower and upper saddles 90 and 91 are compressed together via the elastic element 92. When the upper saddle 91 is engaged with the threaded shaft 88, the coupler 89 is not able to move on the shaft 88.

In an example, the coupler 89 can be connected to the movable slide 26 via a connector piece 94. The connector piece 94 can be attached to a bottom of the movable slide 26. In an example, the connector 94 can be a separate and distinct piece from the movable slide 26. The connector 94 can include a keyed aperture 95 configured to receive a keyed shaft 96 on the upper saddle 91. As such, the upper saddle 91 and the connector 94 can be fixed together. As such, movement of the coupler 89 on the shaft 88 can move the movable slide 26.

When the upper saddle 91 is pulled upward in a direction indicated by arrow A6, the elastic element 92 can stretch, also in the direction of arrow A6, such that the threaded portion 93 of the upper saddle 91 disengages with the threaded shaft 88 and the coupler 89 can move in a forward or backward direction on the threaded shaft 88, thereby moving the movable slide 26 in a forward or backward direction. Once the elastic element 92 is compressed, the threaded portion 93 of the upper saddle can reengage the coupler 89 with the threaded shaft 88, and the coupler 89 can be in a fixed position, and the movable slide 26 can be consequently fixed, until this can be repeated for moving the movable slide 26.

In an example, the connector 94, the shaft 88, the coupler 89 and the motor 97 can be located within an interior portion of the handheld 12 and thus may not be visible to the user.

The direction of rotation and speed of rotation of the shaft 88 by the motor 97 can be controlled by a processor 98 which can be connected to a user interface 99. In an example the user interface 99 can correspond to the forward button 47 and back button 49 of the control panel 41 on the handheld device 12. The movable slide 26 can be manually moved on the handheld device 12, as an alternative to an electronic control with the processor 98 and user interface 99. By pulling the syringe pusher 26 up in a direction of arrow A6, the upper saddle 91 of the coupler 89 can also be pulled up and the threaded portion 93 of the upper saddle 91 can disengage with the shaft 88. Once the proper position of the movable slide 26 is reached, the movable slide 26 can be released and the upper saddle 91 can reengage with the shaft 88 and the lower saddle 90, and thus the coupler 89 can be in a fixed position on the shaft 88.

It is recognized that the connector piece 94 can be excluded from the control system 80 and the movable slide 26 can be directly connected to the upper saddle 91. In an example, the keyed shaft 96 of the upper saddle 91 can engage a keyed aperture formed through a bottom of the movable slide 26. In an example, the keyed shaft 96 can be excluded and the upper saddle 91 can be directly attached to the movable slide 26 or the upper saddle 91 and the movable slide 26 can be a single piece. It is recognized that alternative control mechanisms to those described and shown herein can be used for manual or electronic control of the movable slide 26.

Figure 16:
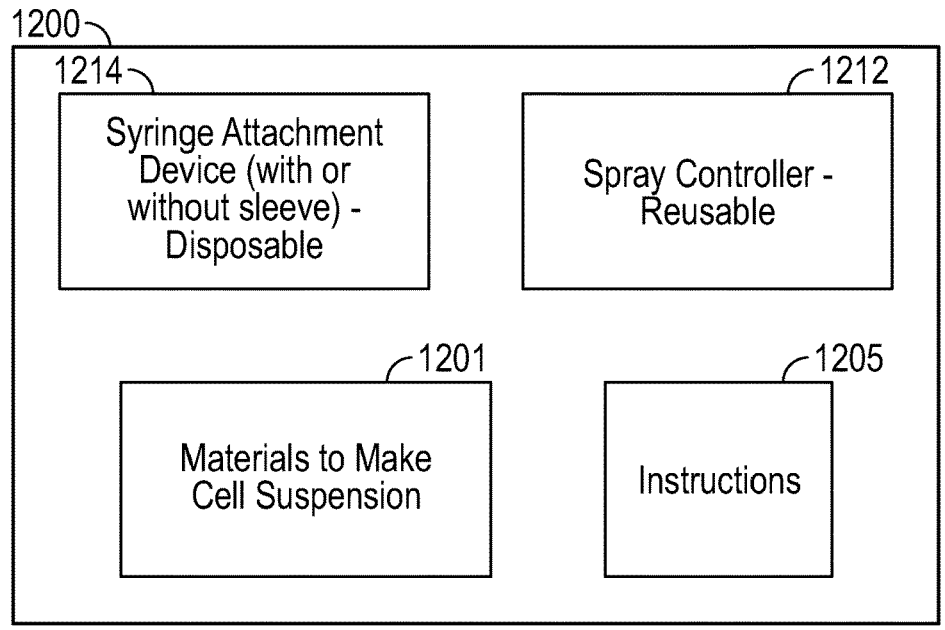
FIG. 16 is a schematic of a kit for treating a wounded area of skin in a living being, in accordance with the present patent application.

FIG. 16 is a schematic of a kit 1200 that can be used for treating a patient with a wound, such as a tissue wound. The kit 1200 can include a spray controller 1212 (also referred to as a handheld device), a syringe attachment device 1214, and materials 1201 used to make a cell suspension, which is an example of a treatment solution delivered from the syringe attachment device 1214. In an example, the syringe attachment device 1214 can include a sleeve or sterile cover, as described above, that can be pre-attached to the syringe attachment device 1214. The spray controller 1212 can be a reusable component. The kit 1200 can include one or more instructions 1205, which can include documentation for preparation of the cell suspension (see below) or for assembly of the syringe attachment device 1214 to the spray controller 1212. Additional instructions can be included and can be related to cleaning or maintenance of one or more of the components of the kit 1200.

It is recognized that the components of the kit 1200 can be provided to a user together or separately. In an example, the kit 1200 can be delivered to the clinician or a user on a cart such that the major components for using a spray deposition system can be in one location. For example, the materials 1201 or instructions 1205 can be included with the kit 1200. In an example, the components of the kit 1200 can be provided separately to the user. For example, the instructions 1205 can be stored electronically by the user and accessed after delivery of other components of the kit 1200.

In an example, at least two cell sources suitable for use in resurfacing and regeneration of damaged tissue can be used with the spray deposition systems described herein: (i) non-autologous cells, including stem cells, and (ii) autologous cells, including the patient's own progenitor cells. The cells can be suspended in solution to form the treatment solution—once formed, the solution can be transported to and contained in a syringe for use in the spray deposition systems described herein—see the treatment solution 18 in the syringe 16, as shown in, for example, FIG. 1.

In an example, a method for preparing an autologous cell suspension can include harvesting tissue from a patient by means known in the art of tissue grafting, which can include taking a tissue biopsy. With the harvesting of the biopsy, consideration can be given to the depth of the biopsy and size of the surface area. The depth and size of the biopsy can influence the ease at which the procedure can be undertaken and the speed with which a patient can recover from the procedure. The chosen donor site may appropriately match the recipient site, for example post-auricular for head and neck, thigh for lower limbs, inner-upper-arm for upper limbs, or palm for sole or vice-versa.

Once a biopsy has been harvested from a patient, the tissue sample can be subjected to physical and/or chemical dissociating means capable of dissociating cellular stratum in the tissue sample. For example, the dissociating means can include physical and/or a chemical disruption. Physical dissociation means can include, for example, scraping the tissue sample with a scalpel, mincing the tissue, physically cutting the layers apart, or perfusing the tissue. Chemical dissociation means can include, for example, digestion with enzymes such as trypsin, dispase, collagenase, trypsin-EDTA, thermolysin, pronase, hyaluronidase, elastase, papain and pancreatin, or a combination thereof. Chemical dissociation can include the use of more than one enzyme and can include the use of two, three, or four enzymes. In one aspect, when more than one enzyme is used the enyzmes are used sequentially. In one aspect, when more than one enzyme is used, they are selected from trypsin, dispase, and collagenase. Non-enzymatic solutions for the dissociation of tissue can also be used. Dissociation of the tissue sample can be achieved by placing the sample in a pre-warmed enzyme solution containing an amount of proteolytic enzyme sufficient to dissociate cellular stratum in the tissue sample.

After the tissue sample has been immersed in the enzyme solution for an appropriate amount of time, the sample can be removed and washed with nutrient solution. The saline/nutrient solution used in the method can be capable of reducing or removing the effect of the enzyme either by dilution or neutralization. When more than one enzyme is used and the tissue sample is exposed to the enzymes sequentially, a washing step can be used after the tissue sample is exposed to each enzyme. The nutrient solution used in the method can also have the characteristics of being (i) free of at least xenogenic serum, (ii) capable of maintaining the viability of the cells until applied to a patient, and (iii) suitable for direct application to a region on a patient undergoing tissue grafting. After application of a suitable saline/nutrition solution to the tissue sample, the cellular stratum of the sample can be separated, permitting the cells capable of reproduction to be removed from the cellular material and suspended in the nutrient solution. Where the tissue sample is skin, the dermis and epidermis can be separated to allow access to the dermal-epithelial junction of both surfaces.

Cells capable of reproduction can then be removed from the separated stratum by any means known in the art. For example, the reproductive cells can be scraped off the surface of the stratum using an instrument such as a scalpel. Cells capable of reproduction within the dermal-epithelial junction can include, but are not limited to, keratinocyte basal cells, Langerhans cells, fibroblasts and melanocytes. Following release of the cells from the tissue sample, the cells can be suspended in the saline/nutrient solution.

In an example, a non-autologous cell suspension can be used to produce cells capable of reproduction for purposes of skin grafting. To procure cells of any source, the cells can be suspended in an aqueous saline/nutrition solution. The solution can be anything physiological from a basic salt solution to a more complex nutrient solution. In an example, the nutrient solution can be free of all serum but contain various salts, such as electrolytes, that resemble the substances found in body fluids. This type of solution can be referred to as physiological saline. Phosphate or other non-toxic substances can also buffer the solution in order to maintain the pH at approximate physiological levels. Suitable nutrient solutions can be based on Ringer-lactate solutions, including, but not limited to, Hartmann's solution, dialysis solutions, and on peripheral intravenous nutrition solutions.

Whether using autologous or non-autologous sources, the volume of solution applied to the tissue sample after harvesting, or by suspending non-autologous cells, can be small, otherwise the suspension may become too fluid, therein providing difficulties in applying the suspension to the graft. The actual volume of solution applied can depend, in part, on a preference of the healthcare practitioner or needs of the patient.

The cell suspension can then be applied using the spray deposition systems described herein. The cell suspension can be transported to the syringe 16 that is received in the syringe attachment device 14. To avoid excessively large cellular congregates in the cellular suspension, the suspension can be filtered, either prior to using the suspension with the device, or by a specific feature of the device. Prior to application with the device or immediately after filtering, the cellular suspension may be diluted to produce an appropriate cell density suitable for the purpose with which the suspension is to be used.

The aqueous cell suspension can be suitable for tissue regeneration and grafting techniques, produced by the method described and the spray deposition systems described herein can provide even cell distribution. Utilizing such a suspension in grafting technology can expand the area or volume of a wound that can be treated quickly by in situ multiplication of a limited number of cells. Cellular multiplication can be encouraged on the patient rather than in an in vitro system, as provided by known methods for cultured epithelial autographs (CEA).

The number and concentration of cells seeded onto a graft site can vary by modifying the concentration of cells in suspension, or by modifying the quantity of suspension that is distributed onto a given area or volume of the graft site. The number and concentration of cells seeded onto the graft site can depend, in part, on the preference of individual surgeons or the needs of the patient.

The composition of cells in the cellular preparation can be comparable to that seen in situ in known CEA cellular preparation. The composition of the cells in the cellular preparation described herein can contain the basal keratinocytes and skin progenitor cells for skin regeneration, which can typically be lost in the CEA method. Whereas conventional methods lose cellular constituents, such as skin progenitor cells, because of selective culture for keratinocytes, the cellular suspension described herein can have a cell composition comparable to the in situ cell population.

The treatment solution and spray deposition systems described herein can be used for treatment of patients requiring a tissue graft. The cellular suspension can be applied to a graft site.

In an example, the reagents and solutions used with the cells can be sterilized before being mixed with the cells and forming the treatment solution.

Reference is made to U.S. application Ser. No. 13/573,003, filed on Aug. 13, 2012, entitled "DEVICE FOR CELL SPRAYING, MANUFACTURING OF THE DEVICE, METHOD FOR SPRAYING WITH THE DEVICE AND A CELL SUSPENSION SPRAYED WITH THE DEVICE", issued as U.S. Pat. No. 9,505,000, and U.S. application Ser. No. 14/136,681, filed on Dec. 20, 2013, entitled "CELL SPRAYING DEVICE, METHOD AND SPRAYED CELL SUSPENSION", issued as U.S. Pat. No. 9,610,430, both of which are incorporated by reference herein in their entirety.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The present application provides for the following exemplary embodiments or examples, the numbering of which is not to be construed as designating levels of importance:

Example 1 provides a spray deposition system comprising a syringe attachment device having a base with a coupling portion and a top portion, and a handheld device. The syringe attachment device comprises a needle adjacent a syringe channel, the syringe channel configured to receive a syringe, and a tube having a discharge end proximate a delivery end of the needle, the tube configured to deliver an air flow. The handheld device can have an upper surface and can include a movable slide disposed on the upper surface. The handheld device can be configured to be coupled to the coupling portion of the syringe attachment device in an assembled position of the system and control delivery of a treatment solution from the syringe. The spray deposition system can comprise a sterile cover positioned to provide an impervious barrier between at least a portion of the syringe attachment device and the handheld device.

Example 2 provides the spray deposition system of Example 1 optionally configured such that the sterile cover is coupled to the syringe attachment device.

Example 3 provides the spray deposition system of Example 1 or 2 optionally configured such that the base of the syringe attachment device is a bottom plate and the top portion of the syringe attachment device is a top plate, and the top and bottom plates are attached together.

Example 4 provides the spray deposition system of Example 3 optionally configured such that the sterile cover is positioned between the top and bottom plates.

Example 5 provides the spray deposition system of Example 1 or 2 optionally configured such that the sterile cover is welded to an outer perimeter of the base of the syringe attachment device.

Example 6 provides the spray deposition system of Example 1 or 2 optionally configured such that the sterile cover is bonded with an adhesive to an outer perimeter of the base of the syringe attachment device.

Example 7 provides the spray deposition system of any of Examples 1-6 optionally configured such that the handheld device is at least partially within a cavity of the sterile cover in the assembled position.

Example 8 provides the spray deposition system of any of Examples 1-7 optionally configured such that the coupling portion of the syringe attachment device includes a bottom surface configured to couple with a top portion of the handheld device in the assembled position.

Example 9 provides the spray deposition system of any of Examples 1-8 optionally configured such that the syringe attachment device includes at least one feature on the coupling portion to engage a corresponding feature on an upper surface of the handheld device.

Example 10 provides the spray deposition system of any of Examples 1-9 optionally configured such that the syringe attachment device includes an air filter coupled to the tube.

Example 11 provides the spray deposition system of any of Examples 1-10 optionally configured such that the syringe attachment device includes an airflow indicator coupled to the tube.

Example 12 provides the spray deposition system of any of Examples 1-11 optionally configured such that the movable slide of the handheld device includes a plunger driver configured to engage a plunger of a syringe disposed in the syringe channel.

Example 13 provides the spray deposition system of Example 12 optionally configured such that the plunger is configured to be electronically positionable or manually positionable by a user of the spray deposition system.

Example 14 provides the spray deposition system of any of Examples 1-13 optionally configured such that the handheld device includes a switch configured to electronically control the movable slide.

Example 15 provides the spray deposition system of Example 14 optionally configured such that the handheld device includes a battery compartment and wherein an electrical contact of the battery compartment is electrically coupled to the electronically movable slide.

Example 16 provides the spray deposition system of any of Examples 1-15 optionally configured such that the movable slide of the handheld device is controlled by a threaded shaft, and a coupler is positioned between and configured for engagement with the movable slide and the threaded shaft. Movement of the coupler on the threaded shaft can correspond to movement of the slide on the handheld device.

Example 17 provides the spray deposition system of any of Examples 1-16 optionally configured such that the sterile cover is attached to the syringe attachment device and extends from sides of the syringe attachment device. The top portion of the syringe attachment device can be exposed and the sterile cover can surround the coupling portion of the syringe attachment device.

Example 18 provides the spray deposition system of Example 17 optionally configured such that the handheld device is inserted into the sterile cover and the sterile cover encloses the handheld device, in the assembled position.

Example 19 provides the spray deposition system of Example 18 optionally configured such that a first end of the sterile cover is closed and the second end of the sterile cover is open, and the second end is sealable after the handheld device is inserted into the sterile cover.

Example 20 provides the spray deposition system of Example 17 optionally configured such that the sterile cover is a sheet open on all sides, the handheld device is covered by the sheet in an assembled position, and the sheet can be closed such that a seal is created between an interior of the sterile cover, containing the handheld device, and exterior of the sterile cover.

Example 21 provides the spray deposition system of any of Examples 1-20 optionally configured such that the handheld device includes a first mark and the sterile cover includes a second mark, and the first and second marks are configured for alignment to determine placement of the sterile cover around at least a portion of the handheld device, in the assembled position.

Example 22 provides the spray deposition system of any of Examples 1-21 optionally configured such that the needle of the syringe attachment device includes a taper fitting.

Example 23 provides the spray deposition system of any of Examples 1-22 optionally configured such that the handheld device includes spray volume indicia.

Example 24 provides the spray deposition system of any of Examples 1-23 optionally configured such that the syringe attachment device is disposable after use and the handheld device is reusable.

Example 25 provides the spray deposition system of any of Examples 1-24 optionally configured such that the syringe removably contains a cell suspension of living cells in a serum-free physiological solution, and the spray deposition system can be configured to spray the cell suspension onto a wounded area of skin on a human subject. The cells can be obtained from the subject's normal skin tissue that has been treated with enzymes thereby causing the cells to release from the dermal-epithelial cell junction.

Example 26 provides the spray deposition system of Example 25 optionally configured such that the cells are uncultured cell types in a ratio comparable to that found in normal skin and comprise basal keratinocytes, Langerhans cells, fibroblasts and melanocytes, and the cells have not been subjected to ex vivo expansion.

Example 27 provides the spray deposition system of Example 25 or 26 optionally configured such that the enzymes include at least one of trypsin, dispase, collagenase, trypsin-EDTA, thermolysin, pronase, hyaluronidase, elastase, papain and pancreatin.

Example 28 provides a method of spray depositing a treatment solution, the method comprising providing a spray deposition system having a syringe attachment device configured to receive a syringe and a handheld device configured to be removably coupled to the syringe attachment device when the system is in an assembled position. The method can further comprise creating a sterile barrier between at least a portion of the syringe attachment device and the handheld device, inserting a syringe into the syringe attachment device, the syringe containing a treatment solution, and spraying the treatment solution from the syringe attachment device.

Example 29 provides the method of Example 28 optionally configured such that creating a sterile barrier includes inserting a portion of the handheld device into a cover attached to the syringe attachment device such that the cover surrounds at least a portion of the handheld device when the handheld device is coupled to the syringe attachment device.

Example 30 provides the method of Example 29 optionally configured such that the syringe attachment device includes top and bottom parts attached together, and the cover is inserted between the top and bottom parts, and wherein the cover extends from sides of the syringe attachment device.

Example 31 provides the method of Example 30 optionally configured such that inserting a portion of the handheld device into the cover includes aligning a marker on the handheld device with a corresponding marker on the cover.

Example 32 provides the method of any of Examples 29-31 optionally configured such that the cover is welded to an outer perimeter of the syringe attachment device.

Example 33 provides the method of any of Examples 29-31 optionally configured such that the cover is bonded with an adhesive to an outer perimeter of the syringe attachment device.

Example 34 provides the method of any of Examples 28-33 optionally configured such that the treatment solution comprises a liquid comprising cells.

Example 35 provides the method of Example 34 optionally configured such that the cells are autologous skin cells.

Example 36 provides the method of any of Examples 28-35 optionally configured such that the treatment solution is contained within a syringe receivable in the syringe attachment device. The method can further comprise coupling a plunger of the syringe with a slide disposed on an upper surface of the handheld device.

Example 37 provides the method of Example 36 optionally configured such that spraying the treatment solution includes depressing the plunger of the syringe with the slide.

Example 38 provides the method of Example 36 or 37 optionally further comprising controlling the slide using at least one of electronic or manual control.

Example 39 provides the method of any of Examples 28-38 optionally further comprising selecting one of a plurality of operational modes for the handheld device.

Example 40 provides the method of any of Examples 28-39 optionally configured such that the syringe attachment device includes tubing that can be connected to the needle and configured to deliver an air flow through the tubing to a discharge end of the tubing located proximate to a delivery end of the needle.

Example 41 provides the method of Example 40 optionally configured such that the syringe attachment device includes an air filter coupled to the tubing.

Example 42 provides the method of any of Examples 28-41 optionally further comprising decoupling the syringe attachment device and the handheld device after spraying the treatment solution.

Example 43 provides the method of any of Examples 28-42 optionally further comprising disposing of the syringe attachment device after spraying the treatment solution, and reusing the handheld device for another spray deposition system.

Example 44 provides the method of any of Example 28-43 optionally configured such that coupling the syringe with the needle of the syringe attachment device includes coupling a tapered fitting.

Example 45 provides the method of any of Examples 28-44 optionally further comprising treating cells of a subject's normal skin tissue with enzymes to cause the cells to release from the dermal-epithelial cell junction, placing the released cells in a serum-free physiological solution to create the treatment solution, and transporting the treatment solution into the syringe.

Example 46 provides the method of Example 45 optionally configured such that the enzymes include at least one of trypsin, dispase, collagenase, trypsin-EDTA, thermolysin, pronase, hyaluronidase, elastase, papain and pancreatin.

Example 47 provides a method of assembling a spray deposition system, the method comprising coupling a syringe attachment device to a handheld device, inserting a syringe at least partially into a syringe channel of the syringe attachment device, and coupling a needle adjacent the syringe channel with the syringe. The method can further comprise coupling a plunger of the syringe with a movable slide of the handheld device, and at least partially surrounding the handheld device with a sterile cover positioned to provide an impervious barrier between at least a portion of the syringe attachment device and the handheld device.

Example 48 provides the method of Example 47 further comprising sterilizing the syringe attachment device prior to coupling the syringe attachment device to the handheld device.

Example 49 provides the method of Example 47 or 48 optionally configured such that at least partially surrounding the handheld device with a sterile cover includes inserting at least a portion of the handheld device into a cavity formed by the sterile cover such that the cover encloses the handheld device when the handheld device is coupled to the syringe attachment device.

Example 50 provides the method of any of Examples 47-49 optionally configured such that at least partially surrounding the handheld device with a sterile cover includes inserting at least a portion of the handheld device into the sterile cover and aligning a marker on the handheld device with a marker on the sterile cover.

Example 51 provides the method of any of Examples 47-50 optionally further comprising treating cells of a subject's normal skin tissue with enzymes to cause the cells to release from the dermal-epithelial cell junction, placing the released cells in a serum-free physiological solution to create a cell suspension, and transporting the cell suspension into the syringe.

Example 52 provides the method of Example 51 optionally configured such that the enzymes include at least one of trypsin, dispase, collagenase, trypsin-EDTA, thermolysin, pronase, hyaluronidase, elastase, papain and pancreatin.

Example 53 provides a kit for treating a wounded area of skin on a living being, the kit comprising a sterile syringe attachment device, a handheld device configured to be removably coupled to the syringe attachment device in an assembled position, one or more materials for making a cell suspension of cells configured to be received in the syringe attachment device and delivered to the wounded area, and instructions for use of the kit. The handheld device can include a feature configured to control delivery of the cells from the syringe attachment device.

Example 54 provides the kit of Example 53 optionally further comprising a sterile cover connected to the sterile syringe attachment device. The sterile cover can surround the handheld device when the handheld device is coupled to the syringe attachment device.

Example 55 provides the kit of Example 53 or 54 optionally configured such that the one or more materials includes at least one of an enzyme or a reagent for isolating cells.

Example 56 provides the kit of Example 55 optionally configured such that the one or more materials includes cells obtained from the living being's normal skin tissue, and the cells have been treated with the enzyme, thereby causing the cells to release from the dermal-epithelial cell junction.

Example 57 provides the kit of Example 55 or 56 optionally configured such that the enzyme includes at least one of trypsin, dispase, collagenase, trypsin-EDTA, thermolysin, pronase, hyaluronidase, elastase, papain and pancreatin.

Example 58 provides the system, methods and kit of any one or any combination of Examples 1-57, which can be optionally configured such that all elements recited are available to use or select from.

Various aspects of the disclosure have been described. These and other aspects are within the scope of the following claims.

The claimed invention is:
1. A spray deposition system, comprising:
a syringe attachment device having a base with a coupling portion and a top portion, the syringe attachment device comprising:
a needle adjacent a syringe channel, the syringe channel configured to receive a syringe; and
a tube having a discharge end proximate a delivery end of the needle, the tube configured to deliver an air flow;
a handheld device having an upper surface and including a movable slide disposed on the upper surface, wherein the handheld device is configured to be coupled to the coupling portion of the syringe attachment device in an assembled position of the system and control delivery of a treatment solution from the syringe; and a sterile cover positioned to provide an impervious barrier between at least a portion of the syringe attachment device and the handheld device,
wherein the sterile cover is coupled to the syringe attachment device.

2. The spray deposition system of claim 1, wherein the base of the syringe attachment device is a bottom plate and the top portion of the syringe attachment device is a top plate, and the top and bottom plates are attached together.

3. The spray deposition system of claim 2, wherein the sterile cover is positioned between the top and bottom plates.

4. The spray deposition system of claim 1, wherein the sterile cover is welded to an outer perimeter of the base of the syringe attachment device.

5. The spray deposition system of claim 1, wherein the sterile cover is bonded with an adhesive to an outer perimeter of the base of the syringe attachment device.

6. The spray deposition system of claim 1, wherein the handheld device is at least partially within a cavity of the sterile cover in the assembled position.

7. The spray deposition system of claim 1, wherein the coupling portion of the syringe attachment device includes a bottom surface configured to couple with a top portion of the handheld device in the assembled position.

8. The spray deposition system of claim 1, wherein the syringe attachment device includes at least one feature on the coupling portion to engage a corresponding feature on an upper surface of the handheld device.

9. The spray deposition system of claim 1, wherein the syringe attachment device includes an air filter coupled to the tube.

10. The spray deposition system of claim 1, wherein the syringe attachment device includes an airflow indicator coupled to the tube.

11. The spray deposition system of claim 1, wherein the sterile cover is attached to the syringe attachment device and extends from sides of the syringe attachment device, and wherein the top portion of the syringe attachment device is exposed and the sterile cover surrounds the coupling portion of the syringe attachment device.

12. The spray deposition system of claim 11, wherein the handheld device is inserted into the sterile cover and the sterile cover encloses the handheld device, in the assembled position.

13. The spray deposition system of claim 12, wherein a first end of the sterile cover is dosed and the second end of the sterile cover is open, and the second end is sealable after the handheld device is inserted into the sterile cover.

14. The spray deposition system of claim 11, wherein the sterile cover is a sheet open on all sides, the handheld device is covered by the sheet in an assembled position, and the sheet can be closed such that a seal is created between an interior of the sterile cover, containing the handheld device, and exterior of the sterile cover.

15. The spray deposition system of claim 1, wherein the handheld device includes a first mark and the sterile cover includes a second mark, and the first and second marks are configured for alignment to determine placement of the sterile cover around at least a portion of the handheld device, in the assembled position.

16. The spray deposition system of claim 1, wherein the syringe removably contains a cell suspension of living cells in a serum-free physiological solution, the spray deposition system is configured to spray the cell suspension onto a wounded area of skin on a human subject, and the cells are obtained from the subject's normal skin tissue that has been treated with enzymes thereby causing the cells to release from the dermal-epithelial cell junction.

17. The spray deposition system of claim 16, wherein the cells are uncultured cell types in a ratio comparable to that found in normal skin and comprise basal keratinocytes, Langerhans cells, fibroblasts and melanocytes, and the cells have not been subjected to ex vivo expansion.

18. The spray deposition system of claim 16, wherein the enzymes include at least one of trypsin, dispose, collagenase, trypsin-EDTA, thermolysin, pronase, hyaluronidase, elastase, papain and pancreatin.

19. A method of spray depositing a treatment solution, the method comprising:

providing a spray deposition system comprising:

a syringe attachment device configured to receive a syringe;

a handheld device configured to be removably coupled to the syringe attachment device when the system is in an assembled position;

creating a sterile barrier between at least a portion of the syringe attachment device and the handheld device via a cover coupled to the syringe attachment device; and inserting a syringe into the syringe attachment device, the syringe containing a treatment solution:

spraying the treatment solution from the syringe attachment device.

20. The method of claim 19, wherein creating a sterile barrier includes inserting a portion of the handheld device into the cover attached to the syringe attachment device such that the sterile cover surrounds at least a portion of the handheld device when the handheld device is coupled to the syringe attachment device.

21. The method of claim 20, wherein the syringe attachment device includes top and bottom parts attached together, and the cover is inserted between the top and bottom parts, and wherein the cover extends from sides of the syringe attachment device.

22. The method of claim 19, wherein the treatment solution comprises a liquid comprising cells.

23. A method of assembling a spray deposition system, comprising:

coupling a syringe attachment device to a handheld device;

inserting a syringe at least partially into a syringe channel of the syringe attachment device;

coupling a needle adjacent the syringe channel with the syringe;

coupling a plunger of the syringe with a movable slide of the handheld device; and at least partially surrounding the handheld device with a sterile cover positioned to provide an impervious barrier between at least a portion of the syringe attachment device and the handheld device, the sterile cover coupled to the syringe attachment device.

24. A kit for treating a wounded area of skin on a living being, the kit comprising:

the spray deposition system of claim 1;

one or more materials for making a cell suspension of cells configured to be received in the syringe attachment device and delivered to the wounded area; and instructions for use of the kit, wherein the handheld device includes a feature configured to control delivery of the cells from the syringe attachment device and an instruction material for the use thereof.

25. The kit of claim 24, wherein the one or more materials includes at least one of an enzyme or a reagent for isolating cells.

26. A spray deposition system, comprising:
a syringe attachment device having a base with a coupling portion and a top portion, the syringe attachment device comprising:
a needle adjacent a syringe channel, the syringe channel configured to receive a syringe; and
a tube having a discharge end proximate a delivery end of the needle, the tube configured to deliver an air flow:
a handheld device having an upper surface and including a movable slide disposed on the upper surface, wherein the handheld device is configured to be coupled to the coupling portion of the syringe attachment device in an assembled position of the system and control delivery of a treatment solution from the syringe; and
a sterile cover positioned to provide an impervious barrier between at least a portion of the syringe attachment device and the handheld device,
wherein the handheld device includes a first mark and the sterile cover includes a second mark, and the first and second marks are configured for alignment to determine placement of the sterile cover around at least a portion of the handheld device, in the assembled position.

27. The spray deposition system of claim 26, wherein the handheld device is at least partially within a cavity of the sterile cover in the assembled position.

* * * * *

UNITED STATES PATENT AND TRADEMARK OFFICE
CERTIFICATE OF CORRECTION

| | | |
|---|---|---|
| PATENT NO. | : 11,040,363 B2 | Page 1 of 1 |
| APPLICATION NO. | : 16/310108 | |
| DATED | : June 22, 2021 | |
| INVENTOR(S) | : Bhogal et al. | |

It is certified that error appears in the above-identified patent and that said Letters Patent is hereby corrected as shown below:

On the Title Page

Page 3, Column 1, item [56], Line 21, delete "Dec. 20, 2013Inter" and insert --Dec. 20, 2013 Inter-- therefor In the Claims Column 27, Line 47, Claim 13, delete "dosed" and insert --closed-- therefor Column 28, Line 9, Claim 18, delete "dispose," and insert --dispase,-- therefor Column 28, Line 25, Claim 19, delete "solution:" and insert --solution;-- therefor Column 29, Line 11, Claim 26, delete "flow:" and insert --flow;-- therefor Signed and Sealed this
Seventh Day of September, 2021

Drew Hirshfeld
*Performing the Functions and Duties of the
Under Secretary of Commerce for Intellectual Property and
Director of the United States Patent and Trademark Office*